United States Patent
Dao et al.

(10) Patent No.: US 11,903,972 B2
(45) Date of Patent: *Feb. 20, 2024

(54) METHODS AND COMPOSITIONS FOR MODULATING PERIPHERAL IMMUNE FUNCTION

(71) Applicant: SanBio, Inc., Mountain View, CA (US)

(72) Inventors: Mo Dao, Huntington Beach, CA (US); Casey C Case, San Mateo, CA (US)

(73) Assignee: SanBio, Inc., Oakland, CA (US)

( * ) Notice: Subject to any disclaimer, the term of this patent is extended or adjusted under 35 U.S.C. 154(b) by 1104 days.

This patent is subject to a terminal disclaimer.

(21) Appl. No.: 16/712,863

(22) Filed: Dec. 12, 2019

(65) Prior Publication Data

US 2020/0113944 A1 Apr. 16, 2020

Related U.S. Application Data

(63) Continuation of application No. 15/494,208, filed on Apr. 21, 2017, now Pat. No. 10,543,234, which is a continuation of application No. 14/298,001, filed on Jun. 6, 2014, now Pat. No. 9,655,927, which is a continuation of application No. 13/441,311, filed on Apr. 6, 2012, now Pat. No. 8,785,190.

(60) Provisional application No. 61/541,248, filed on Sep. 30, 2011, provisional application No. 61/516,637, filed on Apr. 6, 2011.

(51) Int. Cl.
| | |
|---|---|
| *A61K 35/28* | (2015.01) |
| *C12N 5/0783* | (2010.01) |
| *C12N 5/0784* | (2010.01) |
| *C12N 5/0786* | (2010.01) |
| *C12N 5/0775* | (2010.01) |
| *C12N 15/85* | (2006.01) |

(52) U.S. Cl.
CPC ............ *A61K 35/28* (2013.01); *C12N 5/0637* (2013.01); *C12N 5/0639* (2013.01); *C12N 5/0645* (2013.01); *C12N 5/0663* (2013.01); *C12N 15/85* (2013.01); *C12N 2501/2302* (2013.01); *C12N 2501/42* (2013.01); *C12N 2502/1358* (2013.01)

(58) Field of Classification Search
None
See application file for complete search history.

(56) References Cited

U.S. PATENT DOCUMENTS

| | | | |
|---|---|---|---|
| 5,486,359 A | 1/1996 | Caplan et al. | |
| 5,843,780 A | 12/1998 | Thomson | |
| 6,200,806 B1 | 3/2001 | Thomson | |
| 6,280,718 B1 | 8/2001 | Kaufman et al. | |
| 6,602,711 B1 | 8/2003 | Thomson et al. | |
| 6,613,568 B2 | 9/2003 | Kaufman et al. | |
| 6,887,706 B2 | 5/2005 | Zhang et al. | |
| 7,005,252 B1 | 2/2006 | Thomson | |
| 7,029,913 B2 | 4/2006 | Thomson | |
| 7,682,825 B2 | 3/2010 | Dezawa et al. | |
| 8,785,190 B2 | 7/2014 | Dao et al. | |
| RE46,382 E | 5/2017 | Dao et al. | |
| 9,655,927 B2 | 5/2017 | Dao et al. | |
| 2003/0003090 A1 | 1/2003 | Prockop et al. | |
| 2005/0025751 A1 | 2/2005 | Bodmer et al. | |
| 2006/0216276 A1 | 9/2006 | Dezawa et al. | |
| 2010/0034790 A1 | 2/2010 | Dezawa et al. | |
| 2010/0266554 A1 | 10/2010 | Mori et al. | |
| 2010/0310523 A1 | 12/2010 | Dezawa et al. | |
| 2010/0310529 A1 | 12/2010 | Aizman | |
| 2011/0044962 A1 | 2/2011 | Beck | |
| 2011/0136114 A1 | 6/2011 | Case | |
| 2012/0027730 A1 | 2/2012 | Delgado et al. | |
| 2012/0263681 A1 | 10/2012 | Miyoshi et al. | |
| 2014/0286918 A1 | 9/2014 | Dao et al. | |
| 2017/0232042 A1 | 8/2017 | Dao et al. | |

FOREIGN PATENT DOCUMENTS

| | | |
|---|---|---|
| JP | 5932970 | 5/2016 |
| JP | 6134032 | 5/2017 |
| JP | 6392926 | 8/2018 |
| WO | WO 2005/100552 | 10/2005 |
| WO | WO 2008/102460 | 8/2008 |
| WO | WO 2009/023251 | 2/2009 |
| WO | WO 2009/134409 | 11/2009 |
| WO | WO 2010/015929 | 2/2010 |
| WO | WO 2012/154344 | 11/2012 |

OTHER PUBLICATIONS

Nakayamada et al., 2012 Current Opinion in Immunology 2012, 24:297-302 Helper T cell diversity and plasticity.*
Abdallah, et al., "DLKI/F AI Regulates the Function of Human Bone Marrow Mesenchymal Stem Cells by Modulating Gene Expression of Pro-Inflammatory Cytokines and Immune Response-Related Factors," J Biol. Chem., 282:7339-7351 (2007).
Artavanis-Tsakonas et al., "Notch Signaling," Science, 268(5208):225-232 (1995).
Asano, et al., "NOTCH1 Signaling and Regulatory T Cell Function," Journal of Immunology, 180(5):2796-2804 (2008).
Bergmann, et al., "Effect of NF-KB Inhibition on INF-A-Induced Apoptosis and Downstream Pathways in Cardiomyocytes," J. Mol. Cell. Cardiol., 33:1223-1232 (2001).
Bugeon, Laurence et al., "Cutting edge: Notch signaling induces a distinct cytokine profile in dendritic cells that supports T Cell-mediated regulation and IL-2-dependent IL-17 production", J. Immunol., vol. 181, No. 12, Dec. 15, 2008.
Campagnoli et al., "Identification of Mesenchymal Stem/Progenitor Cells in Human Firsttrimester Fetal Blood, Liver, and Bone Marrow," Blood, 98(8):2396-2402 (2001).
Cheng, et al., "NOTCH-1 Regulates NF-KAPP AB Activity in Hemopoietic Progenitor Cells," J. Immunol., 167:4458-4467 (2001).
Chomarat, et al., "IL-6 Switches the Differentiation of Monocytes From Dendritic Cells to Macrophages," Nature Immunol., 1:510-514 (2000).

(Continued)

Primary Examiner — Maria G Leavitt
(74) Attorney, Agent, or Firm — Levine Bagade Han LLP

(57) ABSTRACT

Disclosed herein are cell preparations useful for modulating various peripheral immune functions, methods for making said cell preparations, and methods for their use.

10 Claims, 16 Drawing Sheets

(56) References Cited

OTHER PUBLICATIONS

Coppe, et al., "Senescence-Associated Secretory Phenotypes Reveal Cell-Nonautonomous Functions of Oncogenic RAS and the P53 Tumor Suppressor," PLoS Biol. {2:2853-2868 (2008).
Cutler, et al., "Monocytes Are a Key Intermediary in Mesenchymal Stromal Cell Induced Immunosuppression," Immunolgy, 131(1):118 (2010).
Dao et al., "Comparing the Angiogenic Potency of Naive Marrow Stromal Cells and Notch-Transfected Marrow Stromal Cells," J Translational Medicine, 11:81-91 (2013).
Dezawa et al. "Sciatic Nerve Regeneration in Rats Induced by Transplantation of in Vitro Differentiated Bone-Marrow Stromal Cells," The European Journal of Neuroscience 14(11):1771-1776 (2001).
Dezawa et al., "Specific Induction of Neuronal Cells From Bone Marrow Stromal Cells and Application for Autologous Transplantation," J Clin Invest 113(12):1701-1710 (2004).
Dezawa et al., "Treatment of Neurodegenerative Diseases Using Adult Bone Marrow Stromal Cell-Derived Neurons," Expert Opinion on Biological Therapy 5(4):427-435 (2005).
Djouad, et al., "Mesenchymal Stem Cells Inhibit the Differentiation of Dendritic Cells Through an Interleukin-6-Dependent Mechanism," Stem Cells, 25(8):2025-2032 (2007).
Dogusan, et al., "Macrophages and Stromal Cells Phagocytose Apoptotic Bone Marrowderived B Lineage Cells," J. Immunol., 172:4717-4723 (2004).
Ehebauer et al., "Notch Signaling Pathway," Sci. STKE, 2006(364):cm7 (2006).
Erices et al., "Mesenchymal Progenitor Cells in Human Umbilical Cord Blood," Br. J Haematol., 109(1):235-242 (2000).
Feng, Cheng, "Immunobiological study on marrow-derived mesenchymal stem/progenitor cells modified with mIL-10 gene in a model of murine acute graft-versus-host disease after H-2 haploidentical bone marrow transplantation", Chinese Doctoral Dissertations Full-text Database Medicine and Health Science, No. 04, E060-2, Apr. 15, 2010.
Ferguson, et al., "MMP-2 and MMP-9 Increase the Neurite-Promoting Potential of SCHW ANN Cell Basal Laminae and Are Upregulated in Degenerated Nerve," Mol. Cell. Neurosci., 16:157-167 (2000).
Freund, et al., "Inflammatory Networks During Cellular Senescence: Causes and Consequences," Trends Mal. Med., 16(5):238-246 (2010).
Glavaski-Joksimovic, et al., "Reversal of Dopaminergic Degeneration in a Parkinsonian Rat Following Micrografting of Human Bone Marrow-Derived Neural Progenitors," Cell Transplant 18:801-814 (2009).
Gonzalez-Rey et al., "Human adipose-derived mesenchymal stem cells reduce inflammatory and T cell responses and induce regulatory T cells u in vitro in rheumatoid arthritis," Annals of Rheumatic Diseases, pp. 241-248.
Hilton, et al. "Notch Signaling Maintains Bone Marrow Mesenchymal Progenitors by Suppressing Osteoblast Differentiation," Nature Medicine, 14:306-314 (2008).
Hou et al., "Induction of Umbilical Cord Blood Mesenchymal Stem Cells Into Neuron-Like Cells in Vitro," Int. J Hematol., 78(3):256-261 (2003).
Inhibition | Definition of Inhibition by Merriam-Webster downloaded Sep. 10, 2019, pp. 1-11.
Jiang et al., "Pluripotency of Mesenchymal Stem Cells Derived From Adult Marrow," Nature 418:41-49 (2002).
Jin, et al., "Mesenchymal Stem Cells Cultured Under Hypoxia Escape From Senescence via Down-Regulation of P16 and Extracellular Signal Regulated Kinase," Biochem. Biophys. Res. Commun., 391(3):1471-1476 (2010).
Jones, et al., "Immunosuppression by Mesenchymal Stromal Cells: From Culture to Clinic," Experimental Hematology, 36(6):733-741 (2008).

Kong, et al., "Administration of Bone Marrow Stromal Cells Ameliorates Experimental Autoimmune Myasthenia Gravis by Altering the Balance of THlrrH2/TH17 /TREG Cell Subsets Through the Secretion of TGF-B," J. Neuroimmunol., 207(1-2):83-91 (2009).
Kriete, et al., "Atypical Pathways of NF-Kapp AB Activation and Aging," Exp. Gerontology, 44:250-255 (2009).
Kriete, et al., "Cell Autonomous Expression of Inflammatory Genes in Biologically Aged Fibroblasts Associated With Elevated NF-KAPP AB Activity," Immunity & Ageing, 5:5-12 (2008).
Medzhitov, "Toll-Like Receptors and Innate Immunity," Nat Rev Immunol, 1:135-145 (2001).
Mimura., et al., "Vascular Endothelial Growth Factor Inhibits the Function of Human Mature Dendritic Cells Media TED by VEGF Receptor-2," Cancer Immunol Immunother, 56:761-770 (2007).
Mumm et al., "Notch Signaling: From the Outside in," Dev. Bioi., 228(2):151-165 (2000).
Neurath et al., "Cytokines in inflammatory bowel disease," *Nature Review Immunology*, 14:329-342 (May 2014).
Orjalo, et al., "Cell Surface-Bound IL-la is an Upstream Regulator of the Senescenceassociated IL-6/IL-8 Cytokine Network," PNAS, 106( 40): 17031-17036 (2009).
Oswald, et al., "NF-KAPP AB2 is a Putative Target Gene of ACTN ATED Notch-I via RBP-J Kappa," Mol. Cell. Biol., 18:2077-2088 (1998).
Palucka et al., "Cancer immunotherapy via dendritic cells," Nature Reviews, Cancer, 12:1265-277 (Apr. 2012).
Park, et al., "IL-6 Regulates in Vivo Dendritic Cell Differentiation Through STAT3 Activation," J. Immunol., 173(6):3844-3854 (2004).
Park, et al., Transforming Growth Factor -~! Regulates the Fate of Cultured Spinal Cord-Derived Neural Progenitor Cells, Cell Prolif., 41:248-264 (2008).
*Perricone v. Medicis Pharmaceutical Corp.*, 539 F. Supp. 2d 571-CourtListener.com, p. 1 of 17; downloaded Jul. 6, 2018.
Pittenger et al., "Multilineage Potential of Adult Human Mesenchymal Stem Cells," Science 284(5411):143-147 (1999).
Prockop et al., "Marrow Stromal Cells as Stem Cells for Nonhematopoietic Tissues," Science 276(5309):71-74 (1997).
Rodier, et al., "Persistent DNA Damage Signalling Triggers Senescence-Associated Inflammatory Cytokine Secretion," Nature Cell Biol., 11:973-979 (2009).
Rutz, Sascha et al., "Notch regulates IL-10 production by T helper 1 cells", Proc. Natl. Acid. Sci., vol. 105, No. 9, pp. 3497-3502, Mar. 4, 2008.
Sanchez-Abarca, et al., "Oligodendrocytes Use Lactate as a Source of Energy and as a Precursor of Lipids," Glia, 36:321-329 (2001).
Scaffidi, et al., "Lamina-Dependent Misregulation of Adult Stem Cells Associated With Accelerated Ageing, " Nature Cell Biol., 10:452-459 (2008).
Schober, et al., "GDNF Applied to the MPTP-Lesioned Nigrostriatal System Requires TGFBETA for Its Neuroprotective Action," Neurobiol. Dis., 25:378-391 (2007).
Schober, et al., "Glial Cell Line-Derived Neurotrophic Factor Rescues Target-Deprived Sympathetic Spinal Cord Neurons but Requires Transforming Growth Factor-Beta as Cofactor in Vivo," J. Neurosci., 19:2008-2015 (1999).
Schulte-Herbruggen, et al., "Tumor Necrosis Factor-Alpha and Interleukin-6 Regulate Secretion of Brain-Derived Neurotrophic Factor in Human Monocytes," J. Neuroimmunol., 160:204-209 (2005).
Skihar, et al., "Promoting Oligodendrogenesis and Myelin Repair Using the Multiple Sclerosis Medication Glatiramer Acetate," PNAS USA, 106: 17992-17997 (2009).
Suppressed | Definition of Suppressed by Merriam-Webster Suppressed | Definition of Suppressed by Merriam-Webster Sep. 10, 2019, pp. 1-11.
Suppression | Definition of Suppression by Merriam-Webster Suppressed | Definition of Suppressed by Merriam-Webster, Sep. 10, 2019; pp. 1-10.
Takahashi, et al., "Vascular Endothelial Growth Factor Inhibits Maturation of Dendritic Cells Induced by Lipopol Ysaccharide, but Not by Proinflammatory Cytokines," Cancer Immunol. Immunother., 53(6):543-550 (2004).

(56) References Cited

OTHER PUBLICATIONS

Tate et al., "Human Mesenchymal Stromal Cells and Their Derivative, SB623 Cells, Rescue Neural Cells via Trophic Support Following In Vitro Ischemia," *Cell Transplantation*, vol. 19, pp. 973-984, 2010.

Tolar, et al., "Concise Review: Hitting the Right Spot With Mesenchymal Stromal Cells," Stem Cells 28:1446-1455 (2010).

Van Den Bos, et al., "P21CIP1 Rescues Human Mesenchymal Stem Cells From Apoptosis Induced by Low-Density Culture," Cell & Tissue Res., 293:463-470 (1998).

Van Hall, et al., "Blood Lactate is an Important Energy Source for the Human Brain," J. Cereb. Blood Flow Metab., 29:1121-1129 (2009).

Villoslada, et al., "Immunotherapy for Neurological Diseases," Clin. Immunol., 128(3):294-305 (2008).

Wagner, et al., "Replicative Senescence of Mesenchymal Stem Cells: A Continuous and Organized Process," PLoS One 3(5):e2213 (2008).

Weinstein et al., Journal of Cerebral Blood Flow & Metabolism, 30:15-35, 2010.

Yasuhara, et al., "Notch-Induced Rat and Human Bone Marrow Stromal Cell Grafts Reduce Ischemic Cell Loss and Ameliorate Behavioral Deficits in Chronic Stroke Animals," Stem Cells and Development 18:1501-1514 (2009).

Zhu, et al., "Transforming Growth Factor-Bi Increases Bad Phosphorylation and Protects Neurons Against Damage," J. Neurosci., 12:3898-3909 (2002).

Zuo, et al., "Neuronal Matrix Metalloproteinase-2 Degrades and Inactivates a Neuriteinhibiting Chondroitin Sulfate Proteogl YCAN," J. Neurosci., 18.:5203-5211 (1998).

U.S. Appl. No. 15/494,208, filed Apr. 21, 2017.

U.S. Appl. No. 14/298,001, filed Jun. 6, 2014.

U.S. Appl. No. 13/441,311, filed Apr. 6, 2012.

\* cited by examiner $p<0.05$

METHODS AND COMPOSITIONS FOR MODULATING PERIPHERAL IMMUNE FUNCTION

CROSS-REFERENCE TO RELATED APPLICATIONS

This application is a continuation of U.S. patent application Ser. No. 15/494,208 filed Apr. 21, 2017 (Now U.S. Pat. No. 10,543,234 issued Jan. 28, 2020), which is a continuation of U.S. patent application Ser. No. 14/298,001 filed Jun. 6, 2014 (now U.S. Pat. No. 9,655,927 issued May 23, 2017), which is a continuation of U.S. patent application Ser. No. 13/441,311 filed Apr. 6, 2012 (now U.S. Pat. No. 8,785,190 issued Jul. 22, 2014; reissued as U.S. Patent Number RE 46,382 on May 2, 2017), which claims the benefit of priority to U.S. Provisional Patent Application Nos. 61/516,637 filed Apr. 6, 2011 and 61/541,248 filed Sep. 30, 2011, the contents of all of which are incorporated herein by reference in their entireties.

STATEMENT REGARDING FEDERALLY SUPPORT

Not applicable

FIELD

The disclosure is in the field of immunomodulation (e.g., immunosuppression).

BACKGROUND

Peripheral (i.e., non-CNS) immunity in vertebrates is mediated by two systems: the innate immune system and the adaptive immune system. The innate immune system provides an early, non-specific response to injury and/or infection. By contrast, the adaptive immune system is brought into play later in the process of injury or infection, and is specific to the invading pathogen. The innate immune system, being evolutionarily more ancient, is active in plants, invertebrates and vertebrates, while the adaptive immune system is active in vertebrates only.

As noted above, the innate immune system becomes active immediately upon infection, at the site of infection, and does not depend on prior exposure to the infecting pathogen. It thus provides a set of general defense mechanisms that are not specific to any particular pathogen. Cellular elements of the innate immune system include macrophages, dendritic cells, neutrophils and natural killer (NK) cells. Macromolecular components of the innate immune system include defensin peptides and the complement system. Additional elements of innate immunity include physical barriers to infection (such as the keratinization of the skin, tight junctions between epithelial cells, stomach acid and the mucus secreted by many epithelial tissues) and cell-intrinsic responses such as, for example, phagocytosis (sometimes coupled with lysosomal fusion of phagocytosed material) and degradation of double-stranded RNA.

Activation of the innate immune system is mediated, in part, by recognition of pathogen-associated molecules such as, for example, N-formyl methionine-containing polypeptides, cell wall peptidoglycans, bacterial flagella, lipopolysaccharides, techoic acid, and fungal-specific molecules such as mannan, glucan and chitin. In addition, certain nucleic acid sequences common to microorganisms (such as unmethylated CpG dinucleotides) can trigger innate immune responses. Recognition of such pathogen-associated immunostimulants results in the mounting of an inflammatory response and phagocytosis of the pathogen by macrophages, neutrophils and/or dendritic cells.

Certain of the pathogen-associated immunostimulants noted above occur in repeating patterns called pathogen-associated molecular patterns (PAMPs), which can be recognized by pattern recognition receptors on the surfaces of innate immune system cells. These receptors include soluble members of the complement system and membrane-bound receptors such as members of the Toll-like receptor family (TLRs) and the so-called NOD proteins. The membrane-bound receptors can stimulate phagocytosis and activate programs of gene expression responsible for various innate and adaptive immune responses.

Finally, the innate immune system is involved in activating adaptive immunity, in part by secreting extracellular signaling molecules which stimulate proliferation and differentiation of cells of the adaptive immune system, and also by processing and presenting antigens to cells of the adaptive immune system.

The adaptive immune system, in contrast to the innate immune system, is not activated immediately upon infection, and generates specific, long-lived responses to pathogens. Activation of the adaptive immune system occurs not at the site of injury, but in lymphoid organs, and depends on presentation of antigens by components of the innate immune system to activate cells of the adaptive immune system. The principal cells of the adaptive immune system are B-lymphocytes (B cells), which synthesize and secrete antibodies, and T-lymphocytes (T cells).

There are three major classes of T cells: cytotoxic, helper, and regulatory (or suppressor) T cells. Cytotoxic T cells are able to kill infected host cells. Helper T cells participate in activation of macrophages, dendritic cells, B cells and cytotoxic T cells by secreting cytokines and/or by surface expression of one of a number of different co-stimulatory molecules. There are two types of helper T cells: $T_H1$ cells participate in activation of macrophages, cytotoxic T cells and B cells to provide immunity to intracellular pathogens and secrete the macrophage-activating cytokines interferon gamma (IFN-γ) and tumor necrosis factor alpha (TNF-α). $T_H1$ cells are also capable of stimulating inflammatory responses. $T_H2$ cells help activate B cells to produce antibodies, primarily in response to extracellular pathogens, and secrete the cytokines interleukin 4 (IL4) and interleukin 10 (IL10). Development of a naive helper T cell into a $T_H1$ cell is stimulated by interleukin 12 (IL12); while pathogen-induced expression of the Jagged protein by a dendritic cell will guide a naive helper T cell to develop into a $T_H2$ cell producing IL4, which stimulates antibody production by B cells. Regulatory T cells ($T_{reg}$s) inhibit the function of cytotoxic T cells, helper T cells and dendritic cells, and are unique in expressing the Foxp3 transcription factor. Thus, the interplay between helper T cells and regulatory T cells helps keep the immune response in balance, with sufficient activity to clear an invading pathogen without excessive damage to the host.

A class of lymphocytes in the adaptive immune system known as memory cells retains receptors to a pathogen subsequent to infection and clearance, enabling the host organism to mount a more rapid adaptive immunological response to a subsequent encounter with the same pathogen, and providing the basis for natural or vaccination-induced immunity to many infections diseases. By contrast, the innate immune system does not retain such immunological memory.

Mesenchymal stem cells (MSCs, also known as "marrow stromal cells" or "marrow adherent stem cells"), that have been transfected with a plasmid expressing the Notch intracellular domain (NICD), are useful for the treatment of a number of diseases and disorders of the central and peripheral nervous systems. See, for example, U.S. Pat. No. 7,682,825 (Mar. 23, 2010); US Patent Application Publication No. 2006/0216276 (Sep. 28, 2006); US Patent Application Publication No. 2010/0034790 (Feb. 11, 2010) US Patent Application Publication No. 2010/0310523 (Dec. 9, 2010); International Patent Application Publication No. WO 08/102460 (Aug. 28, 2008); Yasuhara et al. (2009) Stem Cells and Development 18:1501-1513 and Glavaski-Joksimovic et al. (2009) Cell Transplantation 18:801-814.

The ability of these cells, known as SB623 cells, to rescue damaged neural tissue is associated, in part, with their secretion of various trophic factors and their elaboration of various extracellular matrix components. See, for example, US Patent Application Publication No. 2010/0266554 (Oct. 21, 2010) and US Patent Application Publication No. 2010/0310529 (Dec. 9, 2010).

Current cell transplantation therapies have significant disadvantages, including, for example, host peripheral immunological reactions to the transplanted cells. In addition, inflammation is a hallmark of many neurodegenerative diseases, such as, for example, Parkinson's disease and multiple sclerosis. Villoslada et al. (2008) Clin. Immunol. 128:294-305. MSCs have been reported to attenuate peripheral immune activity through mechanisms that include blocking production of antigen-presenting cells and altering the cytokine profile of helper T-cells. Kong et al. (2009) J. Neuroimmunol. 207:83-91. However, MSCs have limited regenerative potential, becoming senescent following ex vivo manipulation. Wagner et al. (2008) PLoS One 3:e2213; Jin et al. (2010) Biochem Biophys Res Commun. 391:1471-1476. Although senescent cells secrete a number of cytokines which could be beneficial for tissue regeneration, the overall senescent cell secretory profile is pro-inflammatory. Rodier et al. (2009) Nature Cell Biol. 11:973-979; Coppe et al. (2008) PLoS Biol. 6:2853-2868; Freund et al. (2010) Trends Mol. Med. 16(5):238-246.

For these and other reasons, there remains a need for methods and compositions for cell transplantation that do not provoke host peripheral immune responses, and/or that reduce inflammatory, and other immune, responses.

SUMMARY

The inventors have identified, within cultures of MSCs that have been transfected with sequences encoding a Notch intracellular domain and their descendants (i.e., SB623 cells), a population of senescent cells. Although SB623 cells have been shown to be capable of treating a number of central nervous system disorders, the present application discloses the surprising ability of SB623 cells to modulate a number of peripheral immune functions. For example, SB623 cells can inhibit human T cell proliferation in both allogeneic and xenogeneic mixed lymphocyte reactions, stimulate IL-10 production by T-cells, and block the differentiation of monocytes to dendritic cells. SB623 cells also inhibit maturation of dendritic cells and, compared to the parental MSCs, SB623 cells exert a greater inhibitory effect on dendritic cell maturation, as evidenced by greater reduction in the surface expression of the co-stimulatory molecule, CD86. SB623 cells can also convert the cytokine profile of a T-cell population from one that is pro-inflammatory to one that is anti-inflammatory. These properties of SB623 cells are additionally surprising and unexpected in light of studies reporting that senescent cells secrete pro-inflammatory cytokines. Orjalo et al. (2009) Proc. Natl. Acad. Sci. USA 106:17031-17036.

Accordingly, SB623 cells, and/or their subpopulation of senescent cells, are useful in a number of therapeutic methods, as exemplified in the following embodiments.

1. A method for peripheral immunosuppression in a subject, the method comprising administering to the subject an effective amount of SB623 cells; wherein said SB623 cells are obtained by (a) providing a culture of mesenchymal stem cells; (b) contacting the cell culture of step (a) with a polynucleotide comprising sequences encoding a Notch intracellular domain (NICD) wherein said polynucleotide does not encode a full-length Notch protein; (c) selecting cells that comprise the polynucleotide of step (b); and (d) further culturing the selected cells of step (c) in the absence of selection.

2. A method for inhibiting a peripheral inflammatory response in a subject, the method comprising administering to the subject an effective amount of SB623 cells; wherein said SB623 cells are obtained by (a) providing a culture of mesenchymal stem cells; (b) contacting the cell culture of step (a) with a polynucleotide comprising sequences encoding a Notch intracellular domain (NICD) wherein said polynucleotide does not encode a full-length Notch protein; (c) selecting cells that comprise the polynucleotide of step (b); and (d) further culturing the selected cells of step (c) in the absence of selection.

3. The method of embodiment 2, wherein the peripheral inflammatory response results from an allogeneic transplantation, ischemia or necrosis.

4. A method for suppressing peripheral T-cell activation in a subject; the method comprising administering to the subject an effective amount of SB623 cells; wherein said SB623 cells are obtained by (a) providing a culture of mesenchymal stem cells; (b) contacting the cell culture of step (a) with a polynucleotide comprising sequences encoding a Notch intracellular domain (NICD) wherein said polynucleotide does not encode a full-length Notch protein; (c) selecting cells that comprise the polynucleotide of step (b); and (d) further culturing the selected cells of step (c) in the absence of selection.

5. The method of embodiment 4, wherein said peripheral T-cell activation comprises expression of CD69 and/or HLA-DR by the T-cells.

6. The method of embodiment 4, wherein said peripheral T-cell activation comprises proliferation of $CD4^+$ T-cells.

7. A method for suppressing the function of peripheral helper T-cells in a subject; the method comprising administering to the subject an effective amount of SB623 cells; wherein said SB623 cells are obtained by (a) providing a culture of mesenchymal stem cells; (b) contacting the cell culture of step (a) with a polynucleotide comprising sequences encoding a Notch intracellular domain (NICD) wherein said polynucleotide does not encode a full-length Notch protein; (c) selecting cells that comprise the polynucleotide of step (b); and (d) further culturing the selected cells of step (c) in the absence of selection.

8. The method of embodiment 7, wherein said peripheral helper T-cell function is cytokine secretion.

9. The method of embodiment 7, wherein said peripheral helper T-cell function is associated with the pathology of rheumatoid arthritis.

10. A method for expanding a population of peripheral regulatory T-cells ($T_{reg}$s) in a subject; the method comprising administering to the subject an effective amount of SB623 cells; wherein said SB623 cells are obtained by (a) providing a culture of mesenchymal stem cells; (b) contacting the cell culture of step (a) with a polynucleotide comprising sequences encoding a Notch intracellular domain (NICD) wherein said polynucleotide does not encode a full-length Notch protein; (c) selecting cells that comprise the polynucleotide of step (b); and (d) further culturing the selected cells of step (c) in the absence of selection.

11. A method for modulating peripheral production of a cytokine in a subject; the method comprising administering to the subject an effective amount of SB623 cells; wherein said SB623 cells are obtained by (a) providing a culture of mesenchymal stem cells; (b) contacting the cell culture of step (a) with a polynucleotide comprising sequences encoding a Notch intracellular domain (NICD) wherein said polynucleotide does not encode a full-length Notch protein; (c) selecting cells that comprise the polynucleotide of step (b); and (d) further culturing the selected cells of step (c) in the absence of selection.

12. The method of embodiment 11, wherein the cytokine is a pro-inflammatory cytokine and production of the cytokine is reduced.

13. The method of embodiment 12, wherein the cytokine is produced by a T cell.

14. The method of embodiment 13, wherein the cytokine is interferon gamma (IFN-γ).

15. The method of embodiment 12, wherein the cytokine is produced by a monocyte.

16. The method of embodiment 15, wherein the cytokine is tumor necrosis factor-alpha (TNF-α).

17. The method of embodiment 11, wherein the cytokine is an anti-inflammatory cytokine and production of the cytokine is stimulated.

18. The method of embodiment 17, wherein the cytokine is interleukin-10 (IL-10).

19. The method of embodiment 18, wherein the cytokine is produced by a T cell or a monocyte.

20. The method of embodiment 19, wherein the T cell is a helper T-cell.

21. The method of embodiment 20, wherein the helper T-cell is a $T_H1$ cell.

22. The method of embodiment 19, wherein the cytokine is produced by a regulatory T-cell.

23. The method of embodiment 22, wherein the regulatory T-cell is a $T_R1$ cell

24. A method for inhibiting the differentiation of a peripheral monocyte to a dendritic cell in a subject; the method comprising administering to the subject an effective amount of SB623 cells; wherein said SB623 cells are obtained by (a) providing a culture of mesenchymal stem cells; (b) contacting the cell culture of step (a) with a polynucleotide comprising sequences encoding a Notch intracellular domain (NICD) wherein said polynucleotide does not encode a full-length Notch protein; (c) selecting cells that comprise the polynucleotide of step (b); and (d) further culturing the selected cells of step (c) in the absence of selection.

25. A method for inhibiting the maturation of a peripheral dendritic cell in a subject; the method comprising administering to the subject an effective amount of SB623 cells; wherein said SB623 cells are obtained by (a) providing a culture of mesenchymal stem cells; (b) contacting the cell culture of step (a) with a polynucleotide comprising sequences encoding a Notch intracellular domain (NICD) wherein said polynucleotide does not encode a full-length Notch protein; (c) selecting cells that comprise the polynucleotide of step (b); and (d) further culturing the selected cells of step (c) in the absence of selection.

26. The method of embodiment 25, wherein maturation comprises an increase in expression of CD86 by the dendritic cell.

27. A method for treating GVHD in a subject; the method comprising administering to the subject an effective amount of SB623 cells; wherein said SB623 cells are obtained by (a) providing a culture of mesenchymal stem cells; (b) contacting the cell culture of step (a) with a polynucleotide comprising sequences encoding a Notch intracellular domain (NICD) wherein said polynucleotide does not encode a full-length Notch protein; (c) selecting cells that comprise the polynucleotide of step (b); and (d) further culturing the selected cells of step (c) in the absence of selection.

28. A method for inhibiting graft rejection in a subject; the method comprising administering to the subject an effective amount of SB623 cells; wherein said SB623 cells are obtained by (a) providing a culture of mesenchymal stem cells; (b) contacting the cell culture of step (a) with a polynucleotide comprising sequences encoding a Notch intracellular domain (NICD) wherein said polynucleotide does not encode a full-length Notch protein; (c) selecting cells that comprise the polynucleotide of step (b); and (d) further culturing the selected cells of step (c) in the absence of selection.

29. A method for treating a peripheral autoimmune disorder in a subject; the method comprising administering to the subject an effective amount of SB623 cells; wherein said SB623 cells are obtained by (a) providing a culture of mesenchymal stem cells; (b) contacting the cell culture of step (a) with a polynucleotide comprising sequences encoding a Notch intracellular domain (NICD) wherein said polynucleotide does not encode a full-length Notch protein; (c) selecting cells that comprise the polynucleotide of step (b); and (d) further culturing the selected cells of step (c) in the absence of selection.

30. The method of embodiment 29, wherein the peripheral autoimmune disorder is selected from the group consisting of multiple sclerosis, ulcerative colitis, chronic obstructive pulmonary disease (COPD), asthma, lupus and Type I diabetes.

31. The method of any of the preceding embodiments, wherein the subject is an experimental animal.

32. The method of any of embodiments 1-30, wherein the subject is a human.

33. A method for modulating a peripheral inflammatory response in a subject, the method comprising administering to the subject an effective amount of SB623 cells; wherein said SB623 cells are obtained by:

(a) providing a culture of marrow adherent stromal cells;

(b) contacting the cell culture of step (a) with a polynucleotide comprising sequences encoding a Notch intracellular domain (NICD) wherein said polynucleotide does not encode a full-length Notch protein;

(c) selecting cells that comprise the polynucleotide of step (b); and (d) further culturing the selected cells of step (c) in the absence of selection for the polynucleotide, such that said marrow adherent stromal cells are induced to form SB623 cells by expression of the NICD.

34. The method of embodiment 33, wherein said modulating comprises inhibition of activation of peripheral T-cells.

35. The method of embodiment 34, wherein said activation of peripheral T-cells comprises expression of CD69 and/or HLA-DR by the T-cells.

36. The method of embodiment 34, wherein said activation of peripheral T-cells comprises proliferation of CD4+ T-cells.

37. The method of embodiment 33, wherein said modulating comprises inhibition of helper T-cell function.

38. The method of embodiment 37, wherein said helper T-cell function is cytokine secretion.

39. The method of embodiment 37, wherein said helper T-cell function is associated with the pathology of rheumatoid arthritis.

40. The method of embodiment 33, wherein said modulating comprises expanding a population of peripheral regulatory T-cells ($T_{reg}$s).

41. The method of embodiment 33, wherein said modulating comprises inhibition of differentiation of a monocyte to a dendritic cell.

42. The method of embodiment 33, wherein said modulating comprises inhibition of the maturation of a dendritic cell.

43. The method of embodiment 42, wherein the maturation comprises an increase in expression of CD86 by the dendritic cell.

44. The method of embodiment 33, wherein the peripheral inflammatory response results from an allogeneic transplantation, ischemia or necrosis.

45. The method of embodiment 33, wherein the peripheral inflammatory response results from graft-versus-host disease (GVHD) or graft rejection.

46. The method of embodiment 33, wherein the peripheral inflammatory response results from an autoimmune disorder.

47. The method of embodiment 46, wherein the autoimmune disorder is selected from the group consisting of multiple sclerosis, ulcerative colitis, chronic obstructive pulmonary disease (COPD), asthma, lupus and Type I diabetes.

BRIEF DESCRIPTION OF THE DRAWINGS

FIG. 3A shows representative FACS data. The peak labeled "M1" represents resting (G0/G1) phase cells. FIG. 3B shows the fraction of cells in the resting phase of the cell cycle, for MSCs and SB623 cells, determined by measuring the area of the M1 peak in FIG. 3A.

FIG. 9A shows representative FACS traces, gating on CFSE and phycoerythrin-labeled anti-CD69, for control unstimulated human T-cells (upper left panel, indicated by "−"); human T-cells stimulated by allogeneic PBMCs (upper right panel, indicated by "MLR"); MLR as before with $10^4$ MSCs (lower left panel, indicated by "MLR+MSC") and MLR as before with $10^4$ SB623 cells (lower right panel, indicated by "MLR+SB623"). FIG. 9B shows quantitation of CD69 expression in MLR cultures. Control, unstimulated T-cell cultures are represented by "Serum;" PBMC-stimulated T-cells in a mixed lymphocyte reaction are represented by "MLR;" a mixed lymphocyte reaction as before in the presence of mesenchymal stem cells is represented by "MSC;" and a mixed lymphocyte reaction as before in the presence of SB623 cells is represented by "SB623." The values for "MSC" and "SB623" are averages of three cultures, each containing MSCs or SB623 cells from different donors.

FIG. 10A shows representative FACS traces for control unstimulated human T-cells (upper left panel, indicated by "T cells alone"); human T-cells stimulated by allogeneic PBMCs (upper right panel, indicated by "MLR"); MLR as before with $10^4$ MSCs (lower left panel, indicated by "MLR+MSC") and MLR as before with $10^4$ SB623 cells (lower right panel, indicated by "MLR+SB623"). FIG. 10B shows quantitation of CSFE dilution in MLR cultures. Compositions of the cultures are as indicated in FIG. 10A.

FIG. 13A shows representative FACS traces, measuring CD4 and CD25, for IL-2-stimulated T-cells ("T cells"), and IL-2-stimulated T-cells co-cultured for seven days with either mesenchymal stem cells ("T cells+MSCs") or SB623 cells ("T cells+SB623 cells"). FIG. 13B shows mean CD4/CD25 expression levels for 5 different matched lots of MSCs and SB623 cells. Note that, for "Donor 1 PBL" a significant increase in $CD4^+$ $CD25^+$ cells is observed ($p<0.05$) in the co-culture with SB623 cells, compared to the co-culture with MSCs.

FIG. 14A shows representative FACS traces for T-cells cultured in the absence of IL-2 (indicated by "RPMI/10% FBS"), T-cells cultured in 10 ng/ml IL-2 (indicated "+IL-2"), T-cells cultured in IL-2 as above and co-cultured with MSCs (indicated "+MSC"), and T-cells cultured in IL-2 as above and co-cultured with SB623 cells (indicated "+SB623").

FIG. 14B shows the mean percentage of FoxP3-expressing T-cells after culture in the presence of IL-2 (indicated "T cells alone") or after co-culture with MSCs ("T cells+MSC") or SB623 cells ("T cells+SB623") in the presence of IL-2. Co-culture was conducted with 3 different matched lots of MSCs and SB623 cells.

FIG. 15A shows representative FACS traces for T-cells cultured in the presence of IL-2 ("T cells alone"), T-cells cultured in IL-2 as above and co-cultured with MSCs (indicated "T cells+MSC"), and T-cells cultured in IL-2 as above and co-cultured with SB623 cells (indicated "T cells+SB623"). Alexa 488 fluorescence, indicative of IL-10 levels, is shown on the abscissa. FIG. 15B shows mean percentage of IL-10-positive cells in co-cultures of T-cells with three different matched lots of MSCs ("T cells+MSC") and SB623 cells ("T cells+SB623"), compared T-cells that were not co-cultured ("T cells alone").

In FIG. 16A, levels of interferon-gamma (IFN-g) are shown in freshly-isolated T-cells prior to culture ("Fresh cells"), T-cells cultured for seven days in the absence of other cells ("Culture control"), T-cells co-cultured with SB623 cells for seven days ("SB623"), and T-cells co-cultured with MSCs for seven days ("MSC"). In FIG. 16B, levels of interleukin-10 (IL-10) are shown in freshly isolated T-cells prior to culture ("Fresh cells"), T-cells cultured for seven days in the absence of other cells ("Culture control"), T-cells co-cultured for seven days with SB623 cells ("SB623"), and T-cells co-cultured for seven days with MSCs ("MSC"). The values for "MSC" and "SB623" are averages of three cultures, each containing MSCs or SB623 cells from a different donor.

FIG. 18A shows representative FACS traces of cells stained for CD 1A and CD 14. Monocytes contain a population of $CD1A^+CD14^+$ dendritic cell precursors (leftmost panel). When monocytes were cultured in the presence of IL-4 and GM-CSF for 7 days, this dendritic cell precursor population is reduced and replaced by a population of $CD1A^+CD14^-$ dendritic cells (second panel from left). When monocytes are co-cultured with MSCs (third panel from left) or SB623 cells (rightmost panel) in the presence of IL-4 and GM-CSF, the $CD1A^+CD14^-$ dendritic cell population is reduced and the $CD1A^+CD14^+$ precursor cell population is increased. FIG. 18B shows mean expression data for monocytes (leftmost pair of bars), monocytes cultured in the presence of IL-4 and GM-CSF for 7 days (second pair of bars from left), monocytes co-cultured with MSCs in the presence of IL-4 and GM-CSF for seven days (third pair of bars from left) or monocytes co-cultured with SB623 cells in the presence of IL-4 and GM-CSF for seven days (right-most pair of bars). Results for the co-culture experiments were obtained from three different matched lots of MSCs and SB623 cells.

FIG. 20A shows the percentage of monocytes in culture that express the inflammatory cytokine TNF-α. FIG. 20B shows the percentage of monocytes in culture that express the anti-inflammatory cytokine IL-10. Monocytes, selected on the basis of surface expression of CD 14, were cultured without supplement ("negative"), with macrophage colony-stimulating factor ("MCSF"), with granulocyte/macrophage colony-stimulating factor ("GMCSF"), with MSCs or with SB623 cells. MSCs and SB623 cells were obtained from three different donors, indicated as D52, D55 and D65 in the figure.

DETAILED DESCRIPTION

Figure 1:
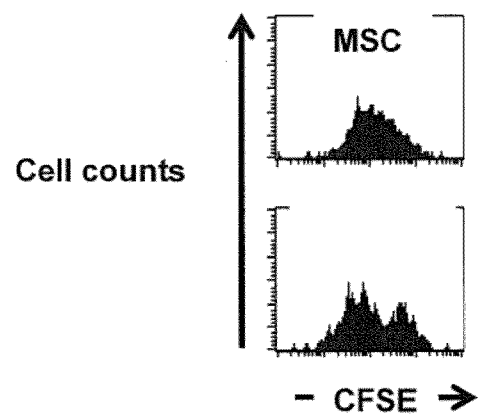
FIG. 1 shows measurements of CFSE dilution, in MSCs and SB623 cells, by flow cytometry.

Practice of the present disclosure employs, unless otherwise indicated, standard methods and conventional techniques in the fields of cell biology, toxicology, molecular biology, biochemistry, cell culture, immunology, oncology, recombinant DNA and related fields as are within the skill of the art. Such techniques are described in the literature and thereby available to those of skill in the art. See, for example, Alberts, B. et al., "Molecular Biology of the Cell," $5^{th}$ edition, Garland Science, New York, N.Y., 2008; Voet, D. et al. "Fundamentals of Biochemistry: Life at the Molecular Level," $3^{rd}$ edition, John Wiley & Sons, Hoboken, N.J., 2008; Sambrook, J. et al., "Molecular Cloning: A Laboratory Manual," $3^{rd}$ edition, Cold Spring Harbor Laboratory Press, 2001; Ausubel, F. et al., "Current Protocols in Molecular Biology," John Wiley & Sons, New York, 1987 and periodic updates; Freshney, R. I., "Culture of Animal Cells: A Manual of Basic Technique," Fifth Edition, Wiley, New York, 2005; and the series "Methods in Enzymology," Academic Press, San Diego, Calif. Standard techniques in immunology are described, for example, in "Current Protocols in Immunology," (R. Coico, series editor), Wiley, updated August 2010.

For the purposes of the present disclosure, the term "peripheral" is used to refer to portions of the body outside of the central nervous system. These include, for example, the bone marrow, peripheral circulation and lymphoid organs.

Preparation of SB623 Cells

Mesenchymal stem cells (MSCs) can be obtained by selecting adherent cells from bone marrow, and can be induced to form SB623 cells by expression of the Notch intracellular domain (NICD) in the adherent cells. In one embodiment, a culture of MSCs is contacted with a polynucleotide comprising sequences encoding a NICD (e.g., by transfection), followed by enrichment of transfected cells by drug selection and further culture. See, for example, U.S. Pat. No. 7,682,825 (Mar. 23, 2010); U.S. Patent Application Publication No. 2010/0266554 (Oct. 21, 2010); and WO 2009/023251 (Feb. 19, 2009); all of which disclosures are incorporated by reference, in their entireties, for the purposes of describing isolation of mesenchymal stem cells and conversion of mesenchymal stem cells to SB623 cells (denoted "neural precursor cells" and "neural regenerating cells" in those documents). See also Example 1, infra.

In these methods, any polynucleotide encoding a Notch intracellular domain (e.g., vector) can be used, and any method for the selection and enrichment of transfected cells can be used. For example, in certain embodiments, a vector containing sequences encoding a Notch intracellular domain also contains sequences encoding a drug resistance marker (e.g. resistance to G418). In these embodiments, selection is achieved, after transfection of a cell culture with the vector, by adding a selective agent (e.g., G418) to the cell culture in an amount sufficient to kill cells that do not comprise the vector but spare cells that do. Absence of selection entails removal of said selective agent or reduction of its concentration to a level that does not kill cells that do not comprise the vector.

Senescence in SB623 Cells

As described above, SB623 cells are derived from MSCs by expression of a NICD in cultured MSCs. Because MSCs that have undergone manipulation in culture often become senescent; the SB623 cells derived therefrom were tested for senescence.

SB623 cells do not form colonies in soft agar, indicating that they are not transformed cells. In addition, when SB623 cells were prelabelled with carboxyfluorescein diacetate succinimidyl ester (CFSE), a cell-permeable dye that is diluted by cell division, a sub-population of cells retained high concentrations of CFSE after 5 days of culture (FIG. 1). This slowly-proliferating (or non-proliferating) sub-population was not observed in MSC cultures. Certain cells in the SB623 cell population were also observed to stain intensely for beta-galactosidase (a marker of cell senescence) and such cells were more plentiful in SB623 cultures than in MSC cultures. These results are consistent with the existence of a pool of non-proliferating, senescent cells in the SB623 cell population.

Figure 2:
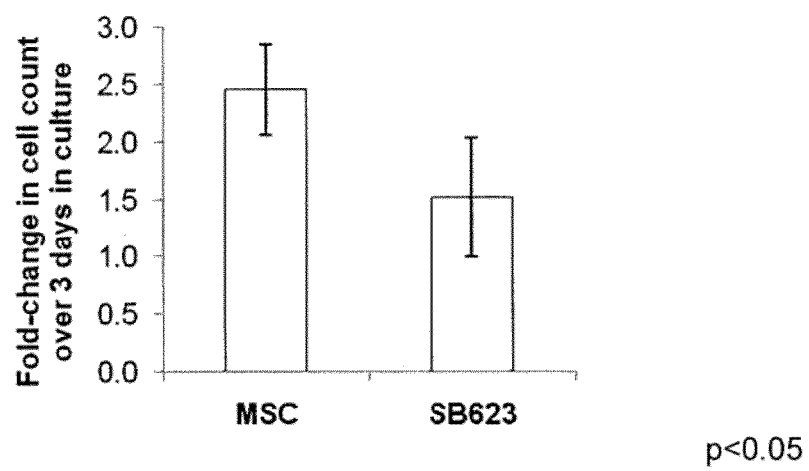
FIG. 2 shows changes in cell count in cultures of MSCs and SB623 cells, determined by Trypan Blue exclusion after three days of culture. Each culture was started with one million cells.

Cell proliferation was measured by plating one million MSCs or SB623 cells and, after three days in culture, measuring viable cells by Trypan Blue exclusion. FIG. 2 shows that a higher number of viable cells were observed in the MSC cultures, indicating a lower proliferative index for the SB623 cells. Cell cycle status was assessed by propidium iodide staining, which revealed a higher proportion of cells in resting phase (G0/G1) in SB623 cultures (FIGS. 3A and 3B), providing further support for a reduced rate of proliferation in SB623 cells.

Figure 4:
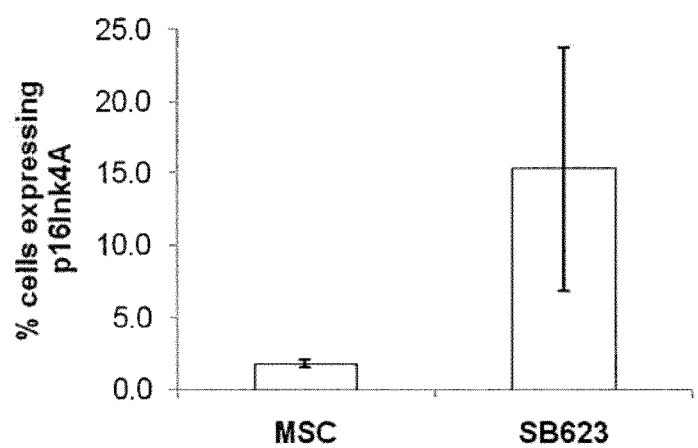
FIG. 4 shows measurements of p16Ink4A levels in MSCs and SB623 cells.

An additional assessment of senescence was conducted by staining populations of SB623 cells for expression of the p16Ink4A protein. p16Ink4A inhibits the progression from the G1 to S phases of the cell cycle and is expressed in senescent cells. FIG. 4 shows that a higher percentage of p16Ink4A-expressing cells were detected in cultures of SB623 cells, compared to MSCs. Moreover, when cells in SB623 cultures that retained high CFSE levels after 5 days of culture were tested for p16Ink4A expression, the subpopulation of SB623 cells expressing p16Ink4A coincided with the fraction containing high CFSE levels. These results, taken together, indicate the existence of a subpopulation of senescent cells within SB623 cultures.

Surface Marker and Cytokine Expression

SB623 cells express a number of surface markers in common with MSCs. These include CD29, CD44, CD73, CD90, CD105 and vascular cell adhesion molecule-1 (VCAM-1 or CD 106). Levels of CD44 and CD73 were higher, and VCAM-1 levels were lower, in SB623 cells compared to MSCs. SB623 cells also express intercellular adhesion molecule-1 (ICAM-1 or CD54), which is not normally expressed by MSCs. See FIGS. 5 and 6. MSCs and SB623 cells do not express the surface markers CD31, CD34 and CD45.

SB623 cells also secrete a number of cytokines and trophic factors. The identity of certain of these factors was determined by blocking protein secretion with Brefeldin A and testing for intracellular cytokines by antibody staining and flow cytometry. These studies showed that SB623 cells produce, among other factors, interleukin 1 α (IL-1 α), interleukin-6 (IL-6), granulocyte/macrophage colony-stimulating factor (GM-CSF), vascular endothelial growth factor-A (VEGF-A) and transforming growth factor beta-1 (TGF β-1). See FIGS. 7 and 8. Amounts of IL-6 and GM-CSF produced by SB623 cells were generally greater than those produced by MSCs.

Because senescent cells have been reported to synthesize and secrete certain growth-stimulatory cytokines and trophic factors (Orjalo et al. (2009) Proc. Natl. Acad. Sci. USA 106:17031-17036), the existence of a population of senescent cells within SB623 cultures suggested the utility of SB623 cell transplantation to support various types of tissue regeneration. However, the secretory profile of senescent cells has also been reported to be pro-inflammatory, which, if it were the case for SB623 cells, might reduce the usefulness of SB623 cells for cell transplantation therapy.

Surprisingly, and despite the presence of a population of senescent cells in SB623 cultures, SB623 cells possess a number of immunosuppressive properties, as disclosed herein. For example, SB623 cells suppress proliferation and activation of T-cells, alter the cytokine profile of T-cells, block the differentiation of monocytes to dendritic cells, and are superior to their parental MSCs at slowing maturation of dendritic cells.

Suppression of T-Cell Activation and T-Cell Proliferation by SB623 Cells

SB623 cells were added to mixed lymphocyte reactions (MLRs) containing $10^5$ CFSE-labeled peripheral blood T-cells and $10^5$ peripheral blood mononuclear cells from an unrelated donor. Levels of CD69, an early marker of T-cell activation, were measured to examine the ability of SB623 cells to modulate T-cell activation. In control mixed lymphocyte reactions, surface expression of CD69 was robustly induced. However, after one day in the presence of $10^4$ SB623 cells, the fraction of $CD4^+$ T-cells (i.e., helper T-cells) in the MLR expressing surface CD69 was significantly reduced. See Example 4.

After five days in the presence of SB623 cells, dilution of CFSE in prelabelled $CD4^+$ T-cells (indicative of cell proliferation) indicated that proliferation of $CD4^+$ T-cells in the MLR was reduced in the presence of SB623 cells. See Example 4. Thus, SB623 cells are capable of suppressing both T-cell proliferation and T-cell activation.

Additional effects of SB623 cells on T-cell function included reduction of surface HLA-DR expression (Example 4 herein), increased production of regulatory T-cells in in vitro cultures of naive T-cells (Example 6 herein) and alteration of cytokine secretion (Examples 7 and 8 herein). SB623 cells were also effective at reducing T-cell proliferation in a xenogenic lymphocyte activation system. See Example 5 herein.

Inhibition of Dendritic Cell Development by SB623 Cells

Differentiation of monocytes into dendritic cells (a type of antigen-presenting cell) and further maturation of dendritic cells can be stimulated in vitro by exposure of monocytes to the cytokines interleukin-4 (IL-4) and granulocyte/macrophage colony-stimulating factor (GM-CSF). This differentiation can be blocked by interleukin-6 (IL-6) or vascular endothelial growth factor (VEGF), both of which are among the cytokines known to be secreted by SB623 cells. See, for example, Tate et al. (2010) Cell Transplant. 19:973-984 and WO 2009/023251.

The inventors show herein that co-culture of monocytes with SB623 cells reduces both the differentiation of monocytes into CD 1a$^+$ dendritic cells and the maturation of dendritic cells to a CD86$^+$ status. See Examples 9 and 10 infra. Because of their abilities to reduce production of new dendritic cells and inhibit the function of existing dendritic cells, SB 623 cells can be used to treat and/or ameliorate graft-versus-host-disease (GVHD) resulting from activation of T-cells by presentation of peptides by antigen-presenting cells, such as dendritic cells.

Because of their various immunosuppressive properties as described herein, SB623 cells can be used in place of other biological and chemical immunosuppressants (e.g., cyclosporine, tacrolimus, sirolimus, interferons, mycophenolic acid, fingolimod, myriocin, azathioprine, mercaptopurine, dactinomycin, mitomycin C, bleomycin, mithramycin, anthracyclines, methotrexate, FK506, cyclophosphamides, nitrosoureas, platinum compounds and glucocorticoids). Moreover, use of immunosuppressive agents is not required to accompany SB623 allogeneic transplantation in cell therapy, e.g., for neuroregeneration and treatment of nervous system disorders.

Progenitor Cells

Progenitor cells, which can be converted to SB623 cells, can be any type of non-terminally differentiated cell. For example, totipotent stem cells as disclosed for example, in U.S. Pat. Nos. 5,843,780; 6,200,806 and 7,029,913 can be used as progenitor cells. Totipotent stem cells can be cultured (e.g., U.S. Pat. Nos. 6,602,711 and 7,005,252) and differentiated into various types of pluripotent cells (e.g., U.S. Pat. Nos. 6,280,718; 6,613,568 and 6,887,706), which can also be used as progenitor cells in the practice of the disclosed methods.

Another exemplary type of progenitor cells are marrow adherent stromal cells (MASCs), also known as marrow adherent stem cells, bone marrow stromal cells (BMSCs) and mesenchymal stem cells (MSCs). Exemplary disclosures of MASCs are provided in U.S. patent application publication No. 2003/0003090; Prockop (1997) Science 276:71-74 and Jiang (2002) Nature 418:41-49. Methods for the isolation and purification of MASCs can be found, for example, in U.S. Pat. No. 5,486,359; Pittenger et al. (1999) Science 284:143-147 and Dezawa et al. (2001) Eur. J. Neurosci. 14:1771-1776. Human MASCs are commercially available (e.g., BioWhittaker, Walkersville, Md.) or can be obtained from donors by, e.g., bone marrow aspiration, followed by selection for adherent bone marrow cells. See, e.g., WO 2005/100552.

MASCs can also be isolated from umbilical cord blood. See, for example, Campagnoli et al. (2001) Blood 98:2396-2402; Erices et al. (2000) Br. J. Haematol. 109:235-242 and Hou et al. (2003) Int. J. Hematol. 78:256-261.

Conversion of MSCs to SB623 cells has been described, for example, in U.S. Pat. No. 7,682,825 (Mar. 23, 2010) and WO 2009/023251 (Feb. 19, 2009); both of which disclosures are incorporated by reference, in their entireties, for the purposes of describing isolation of mesenchymal stem cells and conversion of mesenchymal stem cells to SB623 cells (denoted "neural precursor cells" and "neural regenerating cells" in those documents).

Notch Intracellular Domain

The Notch protein is a transmembrane receptor, found in all metazoans, that influences cell differentiation through intracellular signaling. Contact of the Notch extracellular domain with a Notch ligand (e.g., Delta, Serrate, Jagged) results in two proteolytic cleavages of the Notch protein, the second of which is catalyzed by a γ-secretase and releases the Notch intracellular domain (NICD) into the cytoplasm. In the mouse Notch protein, this cleavage occurs between amino acids gly1743 and val1744. The NICD translocates to the nucleus, where it acts as a transcription factor, recruiting additional transcriptional regulatory proteins (e.g., MAM, histone acetylases) to relieve transcriptional repression of various target genes (e.g., Hes 1).

Additional details and information regarding Notch signaling are found, for example in Artavanis-Tsakonas et al. (1995) Science 268:225-232; Mumm and Kopan (2000) Develop. Biol. 228:151-165 and Ehebauer et al. (2006) Sci. STKE 2006 (364), cm7. [DOI: 10.1126/stke.3642006cm7].

Cell Culture and Transfection

Standard methods for cell culture are known in the art. See, for example, R. I. Freshney "Culture of Animal Cells: A Manual of Basic Technique," Fifth Edition, Wiley, New York, 2005.

Methods for introduction of exogenous DNA into cells (i.e., transfection) are also well-known in the art. See, for example, Sambrook et al. "Molecular Cloning: A Laboratory Manual," Third Edition, Cold Spring Harbor Laboratory Press, 2001; Ausubel et al., "Current Protocols in Molecular Biology," John Wiley & Sons, New York, 1987 and periodic updates.

Autoimmune Disorders and Allergic Reactions

Autoimmune disorders result from an immune response that attacks normal healthy tissue. Exemplary autoimmune disorders include, but are not limited to, amyotrophic lateral sclerosis, ankylosing spondylitis, thrombocytopenic purpura, Hashimoto's thyroiditis, Guillain Barre syndrome, pernicious anemia, dermatosyositis, Addison's disease, Type I diabetes, rheumatoid arthritis, systemic lupus erythematosus ("lupus"), dermatomyositis, Sjogren's syndrome, multiple sclerosis, Myasthenia gravis, polymyositis, biliary cirrhosis, psoriasis, reactive arthritis, Grave's disease, ulcerative colitis, inflammatory bowel disease, vasculitis, Crohn's disease, and celiac disease-sprue (gluten sensitive enteropathy).

Allergies result from an immune hypersensitivity to external substances that would not normally stimulate an immune response. Common allergens include pollen, mold, pet dander and dust. Certain foods and drugs can also cause allergic reactions.

The immunosuppressive properties of SB623 cells, as disclosed herein, make SB623 cells useful for the treatment of autoimmune disorders and allergies.

Formulations, Kits and Routes of Administration

Therapeutic compositions comprising SB623 cells as disclosed herein are also provided. Such compositions typically comprise the cells and a pharmaceutically acceptable carrier.

The therapeutic compositions disclosed herein are useful for, inter alia, immunomodulation (e.g., reducing immune activation) and reversing the progression of various immune disorders. Accordingly, a "therapeutically effective amount" of a composition comprising SB623 cells can be an amount that prevents or reverses immune activation. For example, dosage amounts can vary from about 100; 500; 1,000; 2,500; 5,000; 10,000; 20,000; 50,000; 100,000; 500,000; 1,000,000; 5,000,000 to 10,000,000 cells or more; with a frequency of administration of, e.g., once per day, twice per week, once per week, twice per month, once per month, depending upon, e.g., body weight, route of administration, severity of disease, etc.

Supplementary active compounds can also be incorporated into the compositions. For example, SB623 cells are useful in combination with other immune modulators such as cyclosporine for treatment of, e.g., autoimmune disease or to inhibit transplant rejection and/or GVHD. Accordingly, therapeutic compositions as disclosed herein can contain both SB623 cells and cyclosporine (or any other immunosuppressant). When a composition of SB623 cells is used in combination with another therapeutic agent, one can also refer to the therapeutically effective dose of the combination, which is the combined amounts of the SB623 cells and the other agent that result in immunomodulation, whether administered in combination, serially or simultaneously. More than one combination of concentrations can be therapeutically effective.

Various pharmaceutical compositions and techniques for their preparation and use are known to those of skill in the art in light of the present disclosure. For a detailed listing of suitable pharmacological compositions and techniques for their administration one may refer to texts such as Remington's Pharmaceutical Sciences, 17th ed. 1985; Brunton et al., "Goodman and Gilman's The Pharmacological Basis of Therapeutics," McGraw-Hill, 2005; University of the Sciences in Philadelphia (eds.), "Remington: The Science and Practice of Pharmacy," Lippincott Williams & Wilkins, 2005; and University of the Sciences in Philadelphia (eds.), "Remington: The Principles of Pharmacy Practice," Lippincott Williams & Wilkins, 2008.

The cells described herein may be suspended in a physiologically compatible carrier for transplantation. As used herein, the term "physiologically compatible carrier" refers to a carrier that is compatible with the other ingredients of the formulation and not deleterious to the recipient thereof. Those of skill in the art are familiar with physiologically compatible carriers. Examples of suitable carriers include cell culture medium (e.g., Eagle's minimal essential medium), phosphate buffered saline, Hank's balanced salt solution+/−glucose (HBSS), and multiple electrolyte solutions such as Plasma-Lyte™ A (Baxter).

The volume of a SB623 cell suspension administered to a patient will vary depending on the site of implantation, treatment goal and number of cells in solution. Typically the amount of cells administered to a patient will be a therapeutically effective amount. As used herein, a "therapeutically effective amount" or "effective amount" refers to the number of transplanted cells which are required to effect treatment of the particular disorder; i.e., to produce a reduction in the amount and/or severity of the symptoms associated with that disorder. A therapeutically effective amount further refers to that amount of the composition sufficient to result in full or partial amelioration of symptoms of the relevant medical condition, or an increase in rate of treatment, healing, prevention or amelioration of such condition. For example, in the case of treatment for graft-versus-host disease, transplantation of a therapeutically effective amount of SB623 cells typically results in immunosuppression of grafted cells. If the disorder is graft rejection, for example, a therapeutically effective amount is that number of SB623 which, when transplanted, results in sufficient immunosuppression in the host such that a graft is accepted. Therapeutically effective amounts will vary with the type of disease or disorder, extensiveness of the disease or disorder, and size of the organism suffering from the disease or disorder.

The disclosed therapeutic compositions further include pharmaceutically acceptable materials, compositions or vehicle, such as a liquid or solid filler, diluent, excipient, solvent or encapsulating material, i.e., carriers. These carriers can, for example, stabilize the SB623 cells and/or facilitate the survival of the SB623 cells in the body. Each carrier should be "acceptable" in the sense of being compatible with the other ingredients of the formulation and not injurious to the subject. Some examples of materials which can serve as pharmaceutically-acceptable carriers include: sugars, such as lactose, glucose and sucrose; starches, such as corn starch and potato starch; cellulose and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; alginic acid; pyrogen-free water; isotonic saline; Ringer's solution; ethyl alcohol; phosphate buffer solutions; and other non-toxic compatible substances employed in pharmaceutical formulations. Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Another aspect of the present disclosure relates to kits for carrying out the administration of SB623 cells, optionally in combination with another therapeutic agent, to a subject. In one embodiment, a kit comprises a composition of SB623 cells, formulated in a pharmaceutical carrier, optionally containing, e.g., cyclosporine or another immunosuppressant, formulated as appropriate, in one or more separate pharmaceutical preparations.

Exemplary formulations include, but are not limited to, those suitable for parenteral administration, e.g., intrapulmonary, intravenous, intra-arterial, intra-ocular, intra-cranial, sub-meningial, or subcutaneous administration, including formulations encapsulated in micelles, liposomes or drug-release capsules (active agents incorporated within a biocompatible coating designed for slow-release); ingestible formulations; formulations for topical use, such as eye drops, creams, ointments and gels; and other formulations such as inhalants, aerosols and sprays. The dosage of the compositions of the disclosure will vary according to the extent and severity of the need for treatment, the activity of the administered composition, the general health of the subject, and other considerations well known to the skilled artisan.

In additional embodiments, the compositions described herein are delivered locally. Localized delivery allows for the delivery of the composition non-systemically, thereby reducing the body burden of the composition as compared to systemic delivery. Such local delivery can be achieved, for example, through the use of various medically implanted devices including, but not limited to, stents and catheters, or can be achieved by inhalation, phlebotomy, injection or surgery. Methods for coating, implanting, embedding, and otherwise attaching desired agents to medical devices such as stents and catheters are established in the art and contemplated herein.

EXAMPLES

Example 1: Preparation of MSCs and SB623 Cells

Bone marrow aspirates from adult human donors were obtained from Lonza Walkersville, Inc. (Walkersville, Md.) and plated in at α-MEM (Mediatech, Herndon, Va.) supplemented with 10% fetal bovine serum (Hyclone, Logan, Utah), 2 mM L-glutamine (Invitrogen, Carlsbad, Calif.) and penicillin/streptomycin (Invitrogen). Cells were cultured for three days at 37.degree. C. and 5% $CO_2$, to obtain a monolayer of adherent cells. After removal of non-adherent cells, culture was continued under the same conditions for two weeks. During this time, cells were passaged twice, using 0.25% trypsin/EDTA. A portion of the cells from the second passage were frozen as MSCs.

The remaining cells from the second passage were plated and transfected, using Fugene6 (Roche Diagnostics, Indianapolis, Ind.), with a plasmid containing sequences encoding a Notch intracellular domain operatively linked to a cytomegalovirus promoter (pCMV-hNICD1-SV40-Neo$^R$). This plasmid also contained sequences encoding resistance to neomycin and G418 under the transcriptional control of a SV40 promoter. Transfected cells were cultured at 37.degree. C. and 5% $CO_2$ in the growth medium described in the previous paragraph, supplemented with 100.mu.g/ml G418 (Invitrogen, Carlsbad, Calif.). After seven days, G418-resistant colonies were expanded and the culture was passaged twice. After the second passage, the cells were collected and frozen as SB623 cells.

MSCs and SB623 cells prepared as described herein were thawed as required and used for further study.

Example 2: Proliferative Capacity of MSCs and SB623 Cells

To quantify cell proliferation, one million MSCs or SB623 cells were plated and cultured for three days. Viable cells were counted by trypan blue exclusion on Day 3. FIG. 2 shows that fewer live cells were present in the SB623 cultures, compared to the MSC cultures.

Figure 3A:
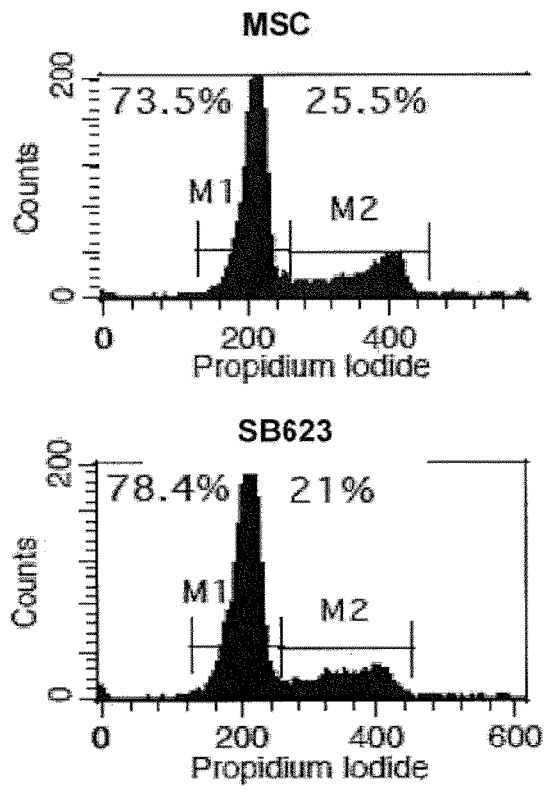
FIGS. 3A and 3B show the results of propidium iodide staining of cultures of MSCs and SB623 cells.
Figure 3B:
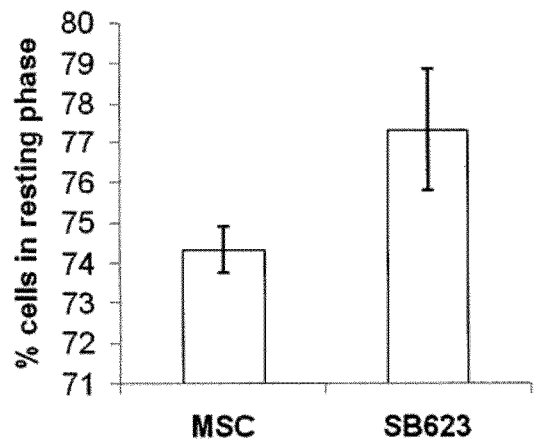

The cell cycle profile of MSC and SB623 cultures was assessed by propidium iodide staining. Propidium iodide is a DNA-intercalating dye that stains cells in the resting phase of the cell cycle more strongly than proliferating cells. After three days of culture, one million MSCs or SB623 cells were fixed in 70% ethanol overnight at 4.degree. C. After two washes in PBS/2% FBS, cells were incubated in one ml of staining buffer (50.mu.g/ml propidium iodide, 50.mu.g/ml RNAse) (Sigma, St. Louis, Mo.) in PBS/2% FBS for 30 min in the dark. Acquisition and analysis were done on a FACSCAlibur™ flow cytometer (BD Biosciences) using a CellQuestPro™ program (BD Biosciences, San Jose, Calif.) on the FL-2 linear channel. FIGS. 3A and 3B show greater propidium iodide staining of SB623 cells, compared to MSCs, indicating a higher fraction of cells in the G0/G1 resting phase of the cell cycle in SB623 cell cultures.

Dilution of the cell-autonomous dye 5-(-6-)carboxyfluorescein diacetate (CFSE) was used as an additional measure of the kinetics of proliferation. For this analysis, an equal number of MSCs and SB623 cells were labeled for 2 min at room temperature with of 5.mu.M of 5-(-6-)carboxyfluorescein diacetate (Invitrogen, Carlsbad, Calif.), then cultured for five days. Flow cytometry acquisition and analysis (for CFSE) were done on a FACSCAlibur™ flow cytometer (BD Biosciences) using the FL-1 log channel. The results, (FIG. 1) show that SB623 cell cultures contained a population of cells with high CFSE content, compared to MSCs, indicating the presence, in SB623 cell cultures, of a population of non-dividing or slowly-dividing cells.

The levels of intracellular p16Ink4A protein in MSCs and SB623 cells were assessed as follows. Cells were cultured for three days, then fixed with 4% paraformaldehyde and permeabilized with PBS containing 0.1% Triton X-100. After two washes in PBS containing 2% fetal bovine serum (PBS/2% FBS), cell pellets were resuspended in 0.2 ml of PBS/2% FBS and divided into two samples. One cell sample was stained with phycoerythrin (PE)-conjugated anti-p16Ink4A antibody (BD Biosciences, San Jose, Calif.) and the other sample was incubated with PE-conjugated mouse IgG as an isotype control. Samples were analyzed by flow cytometry on a FACSCAlibur™ flow cytometer (BD Biosciences) and the data was converted to percentage of cells in the culture expressing p16Ink4A by gating on cells that stained positive for p16Ink4A and negative for IgG. FIG. 4 shows that SB623 cell cultures contain a significantly higher fraction of cells expressing p16Ink4A.

Example 3: Surface Marker and Cytokine Expression by MSCs and SB623 Cells

For measurements of cell surface markers, MSCs or SB623 cells were harvested from culture using 0.25% Trypsin/EDTA (Invitrogen, Carlsbad, Calif.), washed in PBS/2% FBS and resuspended in 1 ml of PBS/2% FBS. Cells were incubated with fluorochrome conjugated antibody to CD29, CD31, CD34, CD44, CD45, CD73, CD90 (all from BD Biosciences, San Jose, Calif.) or CD105 (Invitrogen, Carlsbad, Calif.) for 15 min on ice. Cells were then washed once with PBS/2% FBS and acquired on a FACSCalibur™ flow cytometer (BD Biosciences, San Jose, Calif.). The CellQuestPro™ software (BD Biosciences) was used for data analysis. Results were expressed as dMFI ("delta mean fluorescence intensity"), using IgG as a control; i.e., MFI for IgG was subtracted from the MFI obtained for a given surface marker to obtain the dMFI.

Figure 5:
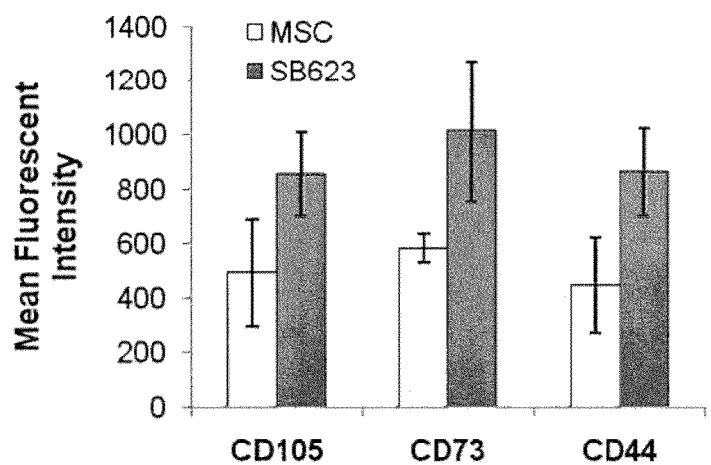
FIG. 5 shows levels of certain surface markers in MSCs and SB623 cells.
Figure 6:
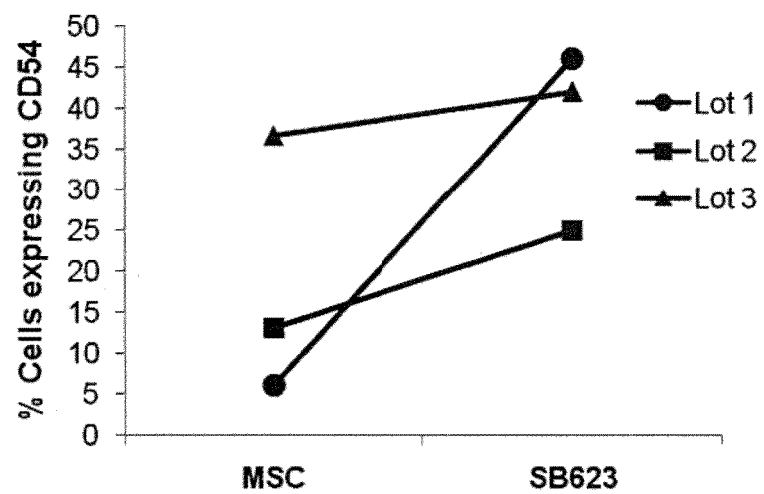
FIG. 6 shows measurements of CD54 expression in MSCs and SB623 cells.

The results are shown in FIGS. 5 and 6. FIG. 5 shows that, although both MSCs and SB623 cells express CD44, CD73 and CD105, SB623 cells consistently express higher levels of these surface markers. FIG. 6 shows that SB623 cells also express consistently higher levels of CD54 than do MSCs.

For detection of intracellular cytokines, cells were cultured for three days and treated with a 1:1,000 dilution of Brefeldin A (eBioscience, San Diego, Calif., final concentration of 3 ug/ml) for six hours prior to harvest. Cells were fixed and permeabilized as described above for measurement of intracellular pInk4A, and incubated with fluorochrome-conjugated antibodies to human GM-CSF (BD), IL-1 alpha (eBioscience, San Diego, Calif.), IL-6 (BD) or TGF β-1 (R&D Systems, Minneapolis, Minn.) for one hour followed by two washes with PBS/2% FBS. Data acquisition and analysis was performed on a BD FACSCalibur™ instrument using CellQuestPro™ software.

Figure 7:
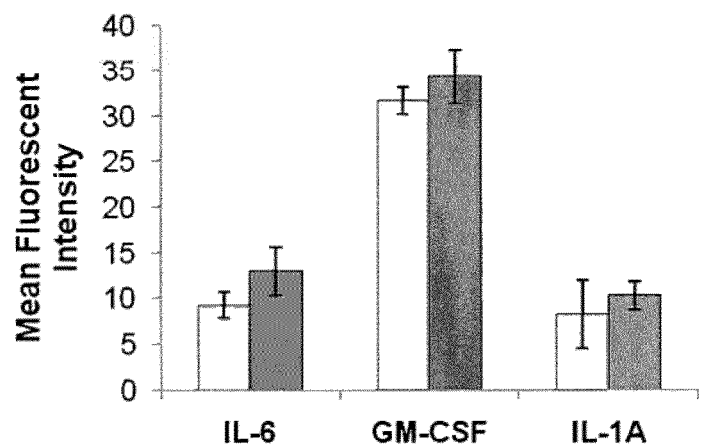
FIG. 7 shows levels of certain cytokines in MSCs and SB623 cells.
Figure 8:
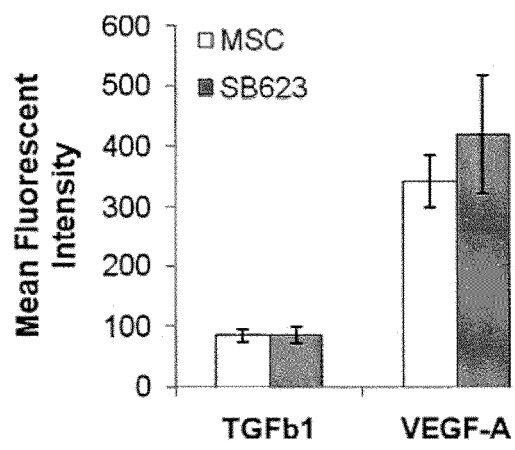
FIG. 8 shows levels of transforming growth factor beta-1 (TGF-β-1) and vascular endothelial growth factor-A (VEGF-A) in MSCs and SB623 cells.

The results of these analyses, presented in FIG. 7 show roughly equivalent levels of expression of IL-1 α, IL-6 and GM-CSF by MSCs and SB623 cells; while FIG. 8 shows that comparable levels of TGF-β-1 and VEGF-A are produced by MSCs and SB623 cells.

Example 4: Allogeneic Mixed Lymphocyte Reaction (Allo-MLR)

Cells for allogeneic mixed lymphocyte reactions were obtained from 10 ml samples of peripheral blood from healthy, unrelated individuals. To obtain responder T-cells, a RosetteSep T-cell enrichment kit (Stemcell Technologies, Vancouver, BC, Canada) was used according to the manufacturer's specifications. Enriched T-cells (responder cells) were labeled for 2 minutes at room temperature with 5 uM 5-(-6-)carboxyfluorescein diacetate (CFSE), obtained from Invitrogen, Carlsbad, Calif. After serum quenching and three washes in PBS, the labeled responder cells were plated, in a volume of 0.1 ml of complete lymphocyte medium (RPMI (Mediatech, Manassas, Va.)+10% FBS (Lonza, Allendale, N.J.) containing $10^5$ cells, in the well of a 96-well U-bottom plate.

To prepare stimulator cells, peripheral blood buffy coat mononuclear cells were recovered after Ficoll™ density gradient centrifugation. Red cell lysis buffer (Sigma-Aldrich, St. Louis, Mo.) was added for 10 min at 37.degree. C.; then the cells were washed twice with PBS/2% heat-inactivated FBS. The mononuclear stimulator cells were either added to the well containing responder cells ($10^5$ cells in a volume of 0.1 ml) or $10^5$ stimulator cells were mixed with $10^4$ SB623 cells or $10^4$ MSCs, centrifuged and the pelleted cells resuspended in a volume of 0.1 ml of complete lymphocyte medium (as described above) which was then added to a well of CFSE-labeled responder cells prepared as described above.

Display of CD69 (an early T-cell activation marker) on the surface of CD4$^+$ T-cells in the culture, two days after initiation of the reaction, was used as an assay for T-cell activation. For analysis of CD69 expression, cells were harvested by pipette after two days, stained with a peridinin chlorophyll protein (PerCP)-conjugated anti-CD69 antibody (eBioscience, San Diego, Calif.), and analyzed using a FACSCalibur™ flow cytometer (Becton, Dickinson & Co., San Jose, Calif.), gating on CD4$^+$ lymphocytes.

For measurements of T-cell proliferation, cells were harvested after seven days of culture and stained with a phycoerythrin (PE)-conjugated anti-CD4 antibody (BD). A BD FACSCalibur flow cytometer was used for data acquisition.

Figure 9A:
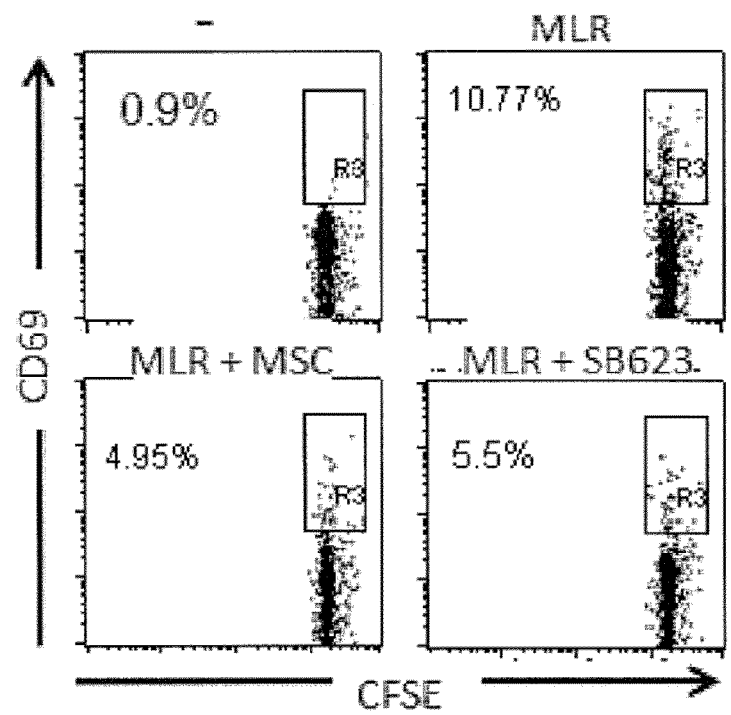
FIGS. 9A and 9B, show the effect of SB623 cells and MSCs on T-cell activation in an allogeneic MLR.
Figure 9B:
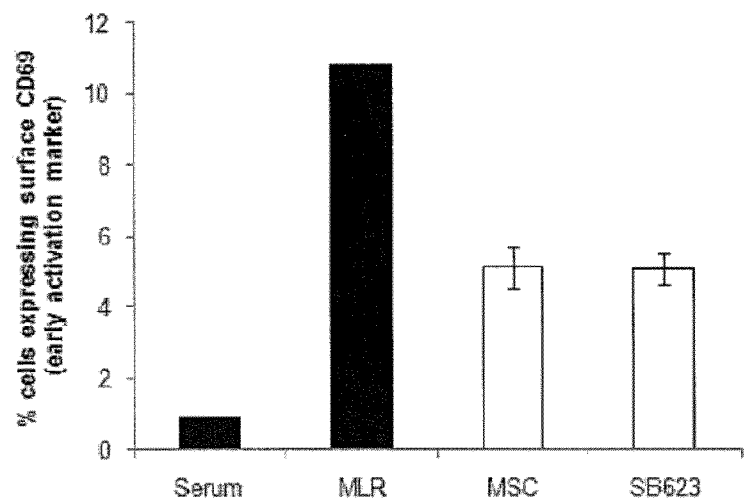

In a control allo-MLR, the fraction of T-cells within the CD4$^+$ population, in which expression of surface CD69 had been induced, was significantly increased after two days (FIGS. 9A and 9B).

The effect of co-culture with MSCs and SB623 cells on T-cell activation in the MLR was also assessed. In these experiments, 10,000 MSCs or 10,000 SB623 cells were added to the culture at the start of the MLR. Under these conditions, the increase in surface CD69-expressing cells that was observed in control cultures after two days was significantly reduced by co-incubation with MSCs or SB623 cells (p<0.05; FIGS. 9A and 9B).

Figure 10A:
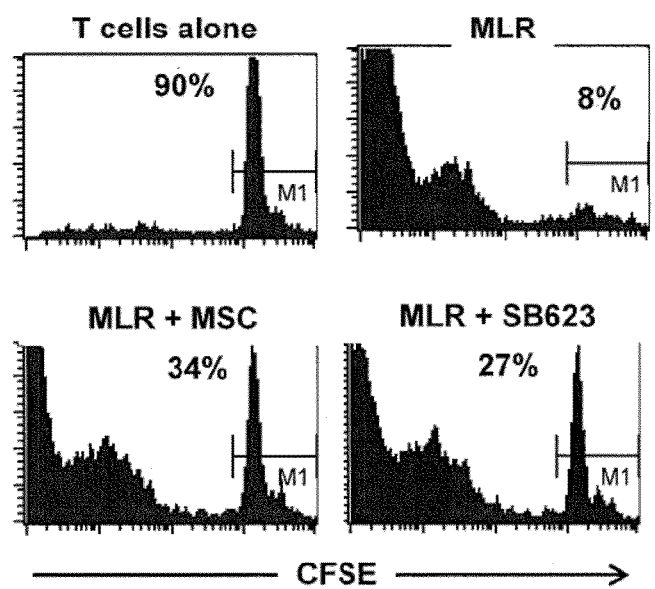
FIGS. 10A and 10B show a comparison of T-cell proliferation rates in an allogeneic MLR, quantitated by measuring CFSE dilution.
Figure 10B:
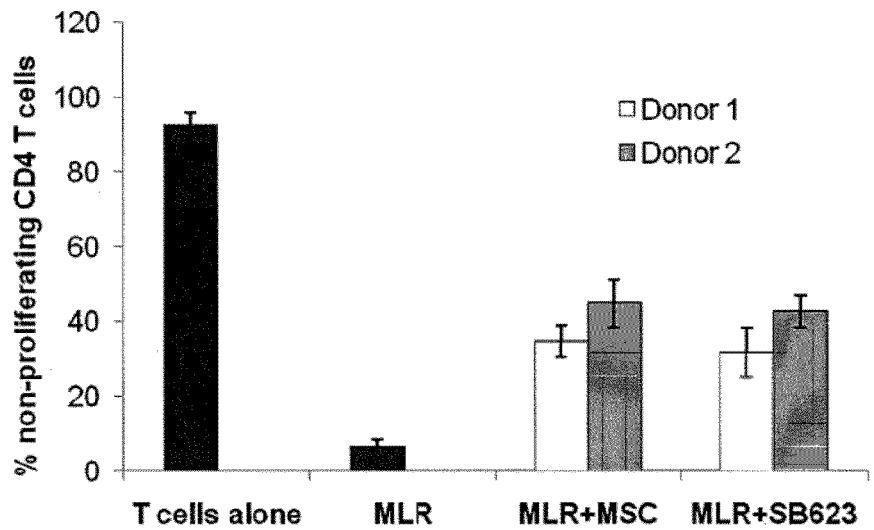

Another measure of T-cell activation, the proliferation rate of CD4+ T-cells was assayed 7 days after initiation of the MLR. For these experiments, cells were harvested from the MLR by pipette and stained with a PE-labeled anti-CD4 antibody. Flow cytometry was conducted using a Becton-Dickinson FACSCalibur™ apparatus, gating on CD4+ cells; and dilution of CSFE was evaluated as an indicator of the proliferation rate of the CD4+ responder T-cells. In a control allo-MLR, more than 80% of the CD4+ responder T-cells had proliferated after seven days. In the presence of SB623 cells or MSCs, T-cell proliferation was significantly reduced (i.e., higher levels of CFSE staining were observed, FIGS. 10A and 10B).

Figure 11:
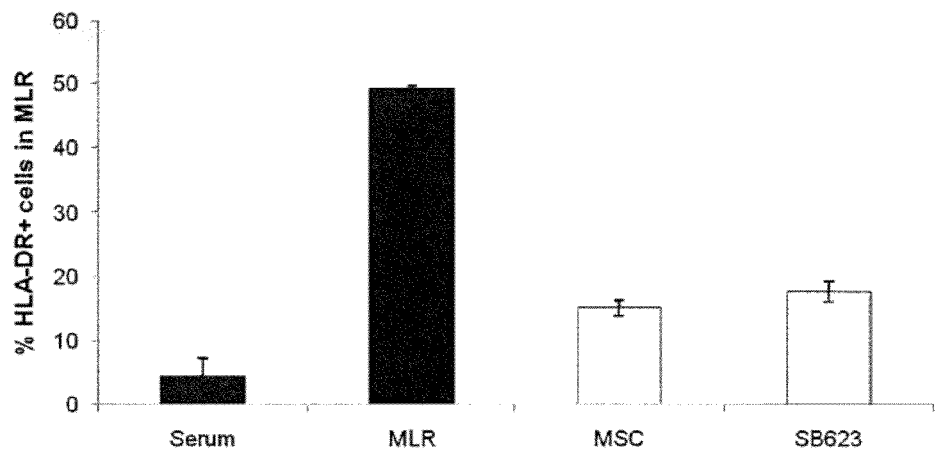
FIG. 11 shows a comparison of HLA-DR expression under different culture conditions. Control, unstimulated T-cell cultures are represented by "Serum;" PBMC-stimulated T-cells in a mixed lymphocyte reaction are represented by "MLR;" a mixed lymphocyte reaction in the presence of mesenchymal stem cells is represented by "MSC;" and a mixed lymphocyte reaction in the presence of SB623 cells is represented by "SB623." The values for "MSC" and "SB623" are averages of three cultures, each containing MSCs or SB623 cells from different donors.

Induction of surface HLA-DR expression is also a measure of T-cell activation. Both SB623 cells and MSCs reduced the percentage of HLA-DR-expressing T-cells in the allo-MLR (FIG. 11).

Thus, by a number of different, independent criteria, SB623 cells suppressed T-cell activation. The ability to block T-cell activation indicates the usefulness of SB623 cells for immunosuppression.

Example 5: Xenogeneic Lymphocyte Activation Reaction

The immunosuppressive properties of SB623 cells were also demonstrated in a xenogenic transplantation model system. Xenogenic lymphocyte reactions were established using Sprague-Dawley rat glial mix cells (comprising astrocytes and microglial cells) as stimulators and human peripheral blood T-cells, labeled with PKH26 according to the manufacturer's instructions (Sigma-Aldrich, St. Louis, Mo.), as responders. To obtain glial mix cells, postnatal day 9 rat brains were harvested and triturated prior to treatment with 0.25% Trypsin for 30 min Cell suspensions were filtered through a 70.mu.M cell strainer and overlaid on Ficoll™ prior to centrifugation. Glial mix cells were cultured in DMEM/F12/10% FBS/pen-strep for 14 days prior to use in the assay. The xenogeneic reaction was performed using cell ratios similar to those used in the allogeneic MLR (100,000 glial mix cells: 100,000 CFSE-labeled human T-cells; and optionally 10,000 MSCs or SB623 cells) over a 5-day period. PKH26 dilution in human CD3-gated T-cells (which includes both CD4$^+$ and CD8$^+$ T-cells) was assessed by flow cytometry.

Figure 12:
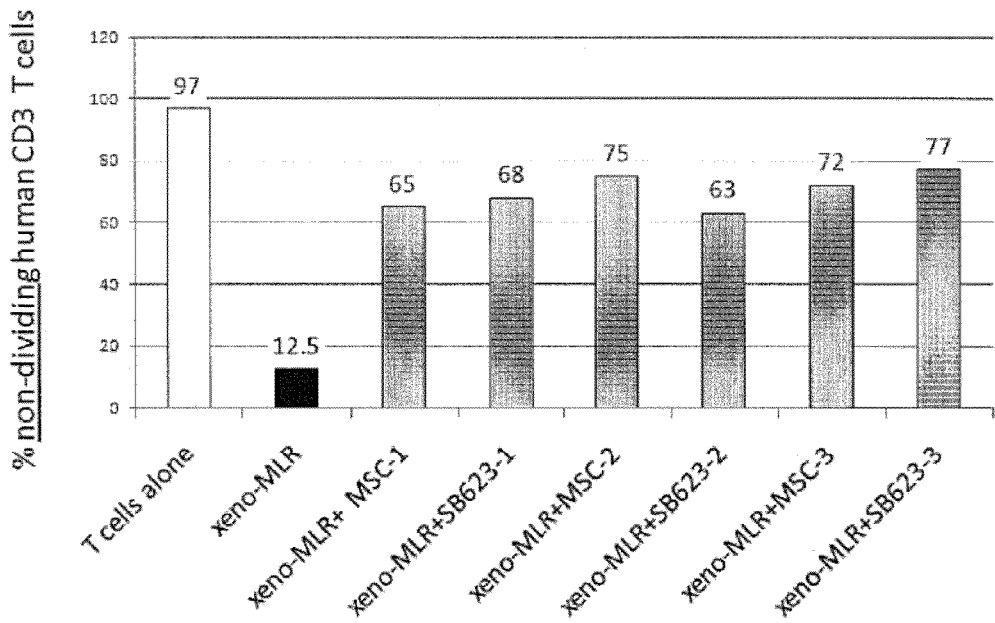
FIG. 12 shows effect of SB623 cells and MSCs on T-cell proliferation in a xenogeneic lymphocyte stimulation reaction. Proliferation was measured by dilution of PKH26, a cell-permeable dye. The percentage of $CD32^+$ T-cells containing PKH26 were measured for unstimulated T-cells ("T cells alone"); T-cells co-cultured with glial mix cells ("xeno-MLR"); T-cells co-cultured with glial mix cells and mesenchymal stem cells ("xeno-MLR+MSC") and T-cells co-cultured with glial mix cells and SB623 cells ("xeno-MLR+SB623"). Preparations of MSCs and SB623 cells were obtained from three different donors, as indicated in the figure.

As in the allogeneic MLR, addition of SB623 cells or MSCs to the xenogeneic system reduced the degree of proliferation of responder T-cells otherwise observed after stimulation by the glial mix cells (FIG. 12). Thus, the immunosuppressive properties of MSCs and SB623 cells are not limited to autologous or allogeneic environments.

Example 6: Effect of SB623 Cells on Development of Regulatory T-Cells

Regulatory T-cells ($T_{reg}$s) are capable of dampening or suppressing immune responses. Accordingly, the ability of SB623 cells to support the generation of $T_{reg}$s was investigated. To this end, enriched T-cells from peripheral blood, purified as described in Example 2, were cultured in the presence of interleukin-2 (IL-2), which has been shown to stimulate the differentiation of naive T-cells into $T_{reg}$s, and the effect of co-culture with MSCs or SB623 cells on this process was assessed. Co-cultures contained a 10:1 ratio of T-cells to SB623 cells or a 10:1 ratio of T-cells to MSCs ($10^5$ T-cells:$10^4$ MSCs or SB623 cells). Coexpression of the surface markers CD4 and CD25, secretion of the cytokine interleukin-10 (IL-10) and intracellular production of the transcription factor FoxP3 were used as markers for $T_{reg}$s.

For these experiments, human T-cells were enriched from peripheral blood using a T-cell isolation kit (StemCell Technologies, Vancouver, Canada) according to the manufacturer's protocol. Enriched T cells were cultured overnight in RPMI-1640/10% heat-inactivated FBS/pen/strep prior to use. On Day-1, 10,000 MSCs or SB623 cells were plated per well in 96-well U-bottom plates. On Day 0 of the co-culture assay, 100,000 enriched T cells were transferred to each well of pre-established MSC or SB623 cell monolayer also containing 10 ng/ml IL-2. As internal controls, T-cell cultures were also maintained in the absence of MSCs or SB623 cells. On day 7, cells were stained for surface CD4 (a helper T-cell marker) and CD25 (the IL-2 receptor alpha chain), and for intracellular FoxP3.

Figure 13A:
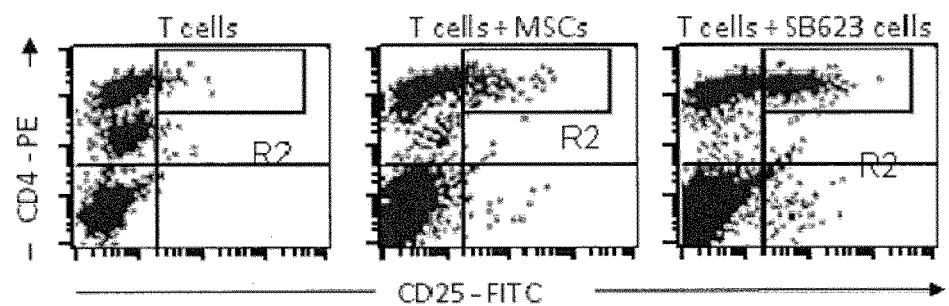
FIGS. 13A and 13B show assays for regulatory T-cells ($T_{reg}$s) in in vitro T-cell cultures, using coexpression of CD4 and CD25 as a marker for $T_{reg}$s.
Figure 13B:
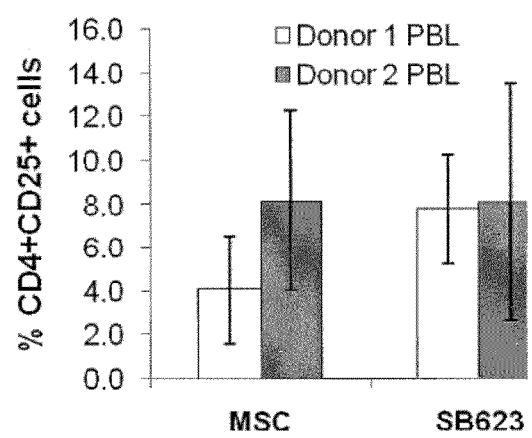

The results of the assays for the surface markers CD4 and CD25 are shown in FIGS. 13A and 13B. Co-culture of SB623 cells with IL-2-stimulated T-cells significantly increased the number of CD4+CD25+ Treg cells (compare left-most and right-most panels of FIG. 13A) and that this stimulation of Treg development was greater when the T-cells were co-cultured with SB623 cells than when they were co-cultured with MSCs (compare center and right panels of FIG. 13A).

Figure 14A:
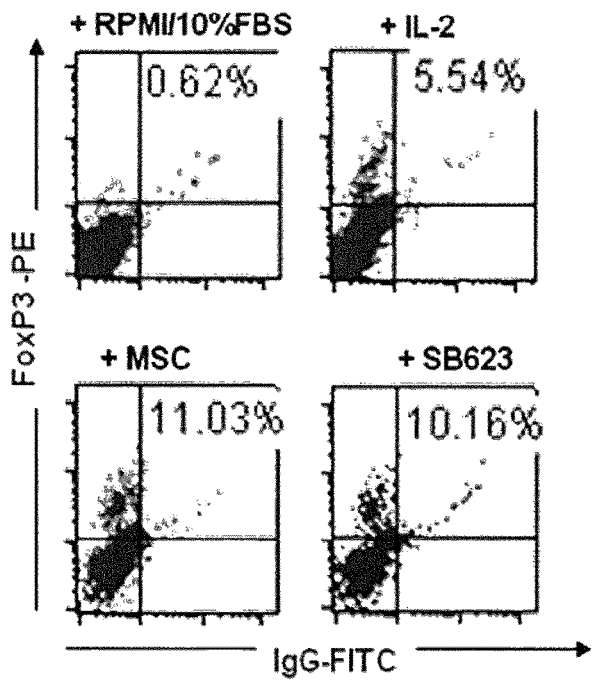
FIGS. 14A and 14B show levels of the FoxP3 transcription factor in T-cells cultured in the presence of IL-2, measured by staining for intracellular FoxP3 with a PE-conjugated anti-FoxP3 antibody, followed by flow cytometry analysis.
Figure 14B:
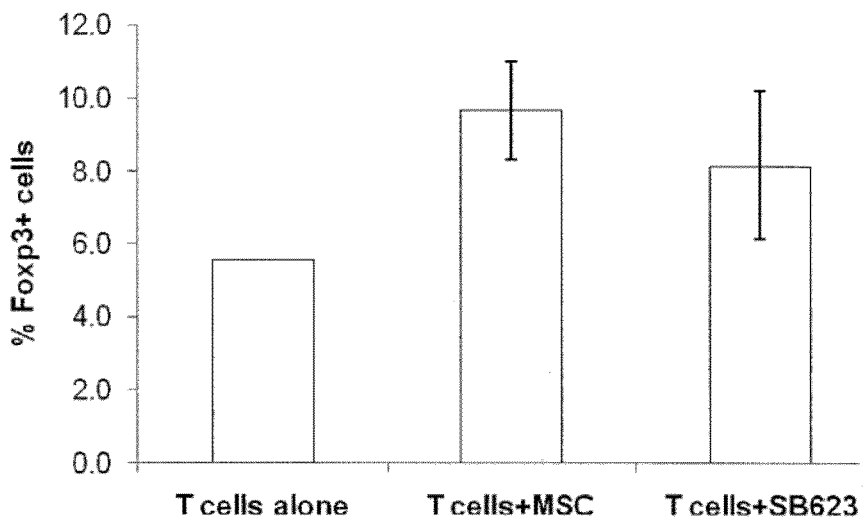

Assays for the forkhead box P3 (FoxP3) protein confirmed these results. FoxP3 is a transcription factor that regulates the development and function of Tregs. Intracellular FoxP3 was detected by culturing or co-culturing T-cells for seven days (as described above), then fixing and permeabilizing cells with CytoFix/Perm (eBioscience, San Diego, Calif.). PE-conjugated anti-FoxP3 antibody (clone PCH101, eBioscience, 1:50 dilution) was used to stain cells for 30 min, and stained cells were analyzed by flow cytometry gating on lymphocytes based on cell size. The results, shown in FIGS. 14A and 14B, demonstrate that co-culture with MSCs and SB623 cells increased FoxP3 expression by T-cells, in the presence of IL-2, compared to its expression in T-cells that were not co-cultured.

One mechanism of immunosuppression by $T_{reg}s$ is through secretion of anti-inflammatory cytokines such as, for example, interleukin-10 (IL-10). Accordingly, the percentage of T-cells producing IL-10 in IL-2-containing T-cell cultures, or in co-cultures with MSCs or SB623s, was determined by staining for intracellular IL-10 with a fluorochrome-conjugated anti-IL-10 antibody after seven days of culture or co-culture.

Accordingly, after 7 days of culture or co-culture, cells were treated with a 1:1,000 dilution of Brefeldin A (eBioscience, San Diego Calif.) (to prevent secretion of extracellular proteins) for six hours, fixed with 2% paraformaldehyde for 15 min, then permeabilized with 0.05% (v/v) Triton-X-100 in PBS/2% FBS for 15 min on ice. Alexa 488-conjugated anti-human IL-10 antibody (eBioscience, San Diego, Calif.) was then added and the cultures were incubated on ice for 30 min Wells were washed twice with 2% fetal bovine serum/0.01% (v/v) Tween 20; cells were acquired by pipette and analyzed using a FACSCalibur™ flow cytometer (Becton, Dickinson & Co., San Jose, Calif.). Data analysis was conducted using CellQuestPro™ software (Becton, Dickinson & Co., San Jose, Calif.).

Figure 15A:
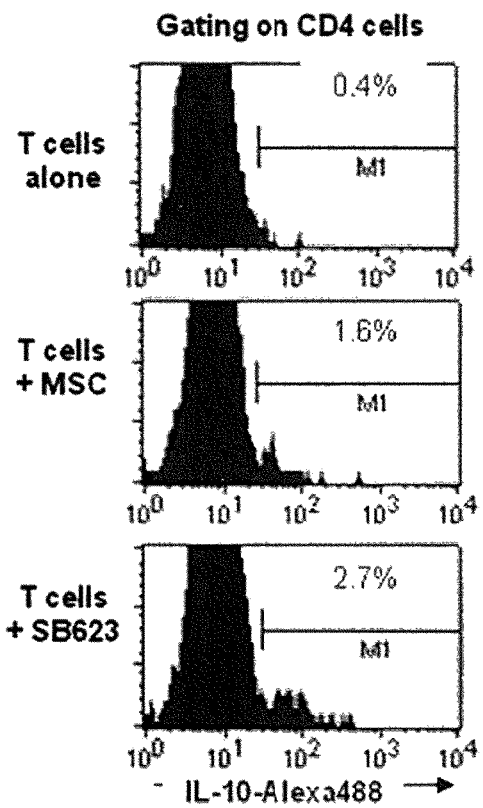
FIGS. 15A and 15B show results of measurements of intracellular IL-10 levels in $CD4^+$ T-cells cultured in the presence of IL-2.
Figure 15B:
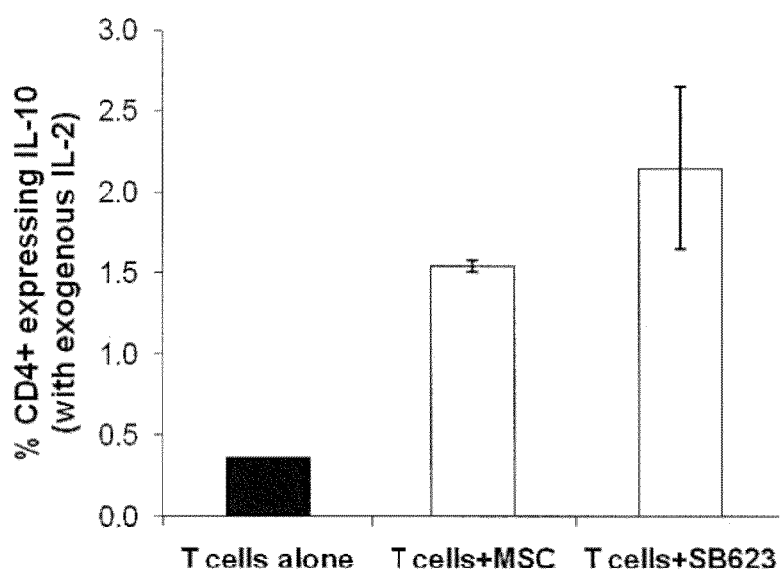

Results of this analysis revealed that T-cells cultured in the presence of IL-2 did not express intracellular IL-10; while low levels of IL-10 were produced by CD4+ T-cells when they were co-cultured with either SB623 cells or MSCs in the presence of IL-2, with slightly more IL-10 being produced by T-cells that were co-cultured with SB623 cells (FIGS. 15A and 15B).

Example 7: Conversion of Pro-Inflammatory to Anti-Inflammatory Cytokine Profile by SB623 Cells The effect of co-culture of MSCs and SB623 cells, on the relative amounts of pro- and anti-inflammatory cytokines produced by T-cells, was assessed by measuring levels of IL-10 (an anti-inflammatory cytokine) and interferon-gamma (IFN-γ, a pro-inflammatory cytokine) in T-cells that had been sub-optimally activated by treatment with phorbol myristate acetate (PMA) and ionomycin. For these experiments, T-cells were enriched from peripheral blood and cultured, or co-cultured with MSCs or SB623 cells, as described above (Example 6), except that culture was conducted in the absence of IL-2. On Day 7, non-activating doses of 25 ng/ml of phorbol 12-myristate 13-acetate (PMA)/0.5.mu.M ionomycin (Io) (both from Sigma-Aldrich, St Louis, Mo.) were added in the presence of 3.mu.g/ml Brefeldin A (eBioscience, San Diego, Calif.) and, 6 hours later, cells were harvested and analyzed for intracellular expression of IL-10 and IFN-gamma. The non-activating doses of PMA and ionomycin used in these experiments did not induce T-cell proliferation, but were sufficient to induce cytokine synthesis by T-cells. IL-10 levels were measured using an Alexa 488-conjugated anti-human IL-10 antibody (eBioscience, San Diego, Calif.) as described in Example 6. IFN-γ levels were measured by FACS, using a PE-labeled anti-human IFN-γ antibody (eBioscience, San Diego, Calif.).

Figure 16A:
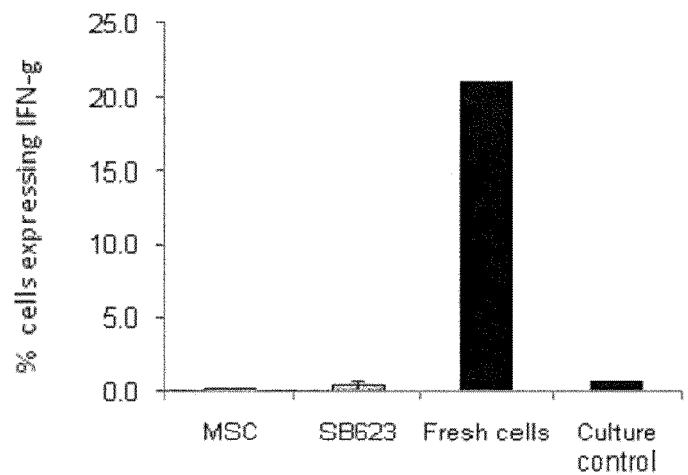
FIGS. 16A and 16B, show levels of cytokines in T-cells cultured in the absence of IL-2 and in the presence of non-maximally-inducing levels of PMA and ionomycin.
Figure 16B:
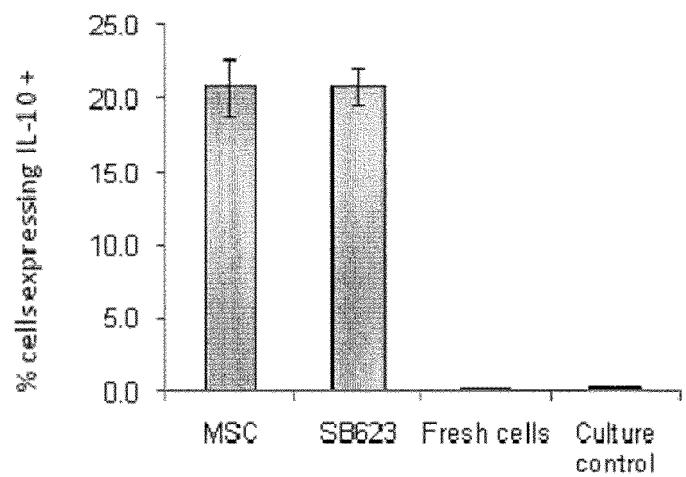

The results of this analysis are shown in FIGS. 16A and 16B. More than 20% of freshly-isolated T-cells expressed IFN-γ, while less than 1% expressed IL-10, after suboptimal stimulation with PMA/ionomycin (i.e., of the cells that expressed either IFN-γ or IL-10, over 95% expressed IFN-γ and less than 5% expressed IL-10). However, after 7 days' co-culture with either SB623 cells or MSCs, of the cells expressing either IFN-γ or IL-10, more than 95% expressed IL-10, while less than 5% expressed IFN-γ. Thus, co-culture with either MSCs or SB623 cells converted the T-cell secretome from one that was pro-inflammatory to one that was anti-inflammatory.

The secretion of the inflammatory cytokine IFN-γ is a characteristic of the $T_H1$ subset of helper T-cells; while IL-10 secretion is characteristic of $T_H2$ cells and $T_{reg}$ cells. Thus, the shift from IFN-γ secretion to IL-10 secretion, observed upon co-culture of naive T-cells with SB623 cells or MSCs, is consistent with conversion of a population rich in $T_H1$ cells into one that contains a large amount of $T_H2$ cells, $T_{reg}$ cells, or both. This result also indicates that co-culture with SB623 cells, or MSCs, directed the differentiation of T-cells from an inflammatory population (characterized by $T_H1$ cells) to an more anti-inflammatory population (characterized by $T_H2$ cells and/or $T_{reg}$ cells), in part through altering cytokine production by the T-cells.

Example 8: Effect of MSC and SB623 Cell Co-Culture on Production of IL-17 by T-Cells Two of the cytokines known to be secreted by MSCs and SB623 cells, TGF β-1 and IL-6 (see Example 3, above) are also known to play a role in the development of Th17 helper T-cells (i.e., helper T cells that secrete IL-17). Accordingly, T-cells were cultured in the presence of IL-23, which is known to stimulate the development of Th17 helper T-cells, and the effect of co-culture with MSCs or SB623 cells, on Th17 cell number, was determined.

Figure 17:
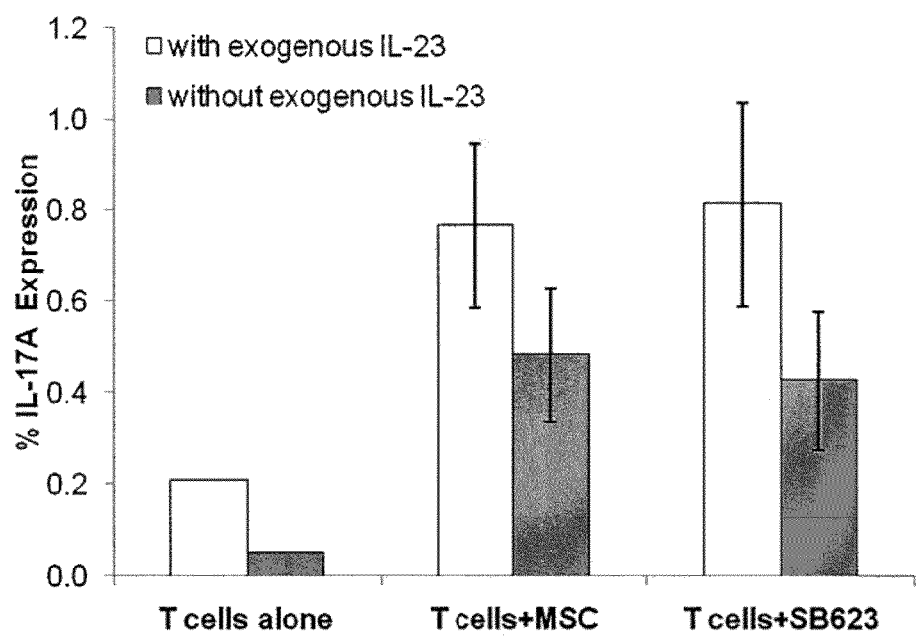
FIG. 17 shows levels of IL-17 in IL-23-stimulated T-cells. Percent expression was determined by flow cytometry after staining cells for IL-17 with a fluorescent antibody. T-cells were cultured with or without IL-23, as indicated, and alone or in co-culture with MSCs or SB623 cells, as indicated.

For these experiments, human T-cells were isolated and cultured as described in Example 7, above, with the addition of 10 ng/ml of IL-23 (Peprotech, Rocky Hill, N.J.) to the cultures. After treatment with Brefeldin A for 6 hours, cells were harvested, fixed and permeabilized as described in Example 7, stained with a PE-conjugated anti-IL17 antibody (eBioscience) and analyzed by flow cytometry. The results indicated that culture of T-cells in the presence of IL-23 increased the number of IL-17-expressing cells. In addition, co-culture of T-cells with MSCs or SB623 cells resulted in a small increase in the number of IL-17-expressing cells, in both the absence and presence of IL-23. (FIG. 17).

Example 9: Inhibition of the Differentiation of Monocytes into Dendritic Cells by Co-Culture with SB623 Cells The normal course of development of monocytes (expressing CD14) into dendritic cells (which express CD1a) can be recapitulated in vitro by culturing monocytes in the presence of interleukin-4 (IL-4) and granulocyte/macrophage colony-stimulating factor (GM-CSF). MSCs, when co-cultured with monocytes in vitro, are able to block the differentiation of monocytes into dendritic cells, an effect that is mediated, in part, by secretion of interleukin-6 (IL-6) by MSCs. Chomarat et al. (2000) Nature Immunology 1:510-514; Djouad et al. (2007) Stem Cells 25:2025-2032. SB623 cells also secrete IL-6. See U.S. Patent Application Publication No. 2010/0266554 (Oct. 21, 2010). VEGF, which is also secreted by MSCs and SB623 cells, is also involved in dendritic cell differentiation. Therefore, the effect of SB623 cells on monocyte differentiation was investigated.

Peripheral blood was collected from healthy donors and subjected to density gradient centrifugation using Ficoll-Paque™ (GE Healthcare, Piscataway, N.J.). Mononuclear cells were recovered by aspirating the buffy coat, resuspended in RPMI/10% fetal bovine serum and plated. After overnight culture at 37.degree. C., 5% $CO_2$, non-adherent cells were washed off and adherent monocytes were recovered using 0.25% trypsin/2 mM EDTA. Staining with FITC-conjugated anti-human CD14 antibody (Becton, Dickinson & Co., San Jose, Calif.) indicated that over 90% of the cells in these preparation were monocytes).

Monocytes were cultured in RPMI-1640 (Meidatech, Manassas, Va.) containing 10% fetal bovine serum (Lonza, Allendale, N.J.), 2 mM L-glutamine, 2 mM L-sodium pyruvate, 100 Units/ml penicillin, 100 ug/ml streptomycin, 40 ng/ml GM-CSF (Peprotech, Rocky Hill, N.J.) and 20 ng/ml IL-4 (Peprotech, Rocky Hill, N.J.). Co-culture with SB623 cells (or MSCs, as control) was conducted at a 10:1 ratio of monocytes to SB6323 cells (or MSCs); i.e., 100,000 monocytes to 10,000 SB623 cells or MSCs. After 7 days of culture (or co-culture), a portion of the cells were harvested using trypsin/EDTA (as above) and incubated with PE-conjugated anti-CD 14 antibody and FITC-labeled anti-CD1a antibody (both from eBioscience, San Diego, Calif.). Acquisition and analysis were performed using a FACSCalibur™ cell sorter using CellQuestPro™ software (both from Becton, Dickinson & Co., San Jose, Calif.). Another portion of the cultures were observed by phase-contrast microscopy.

Figure 18A:
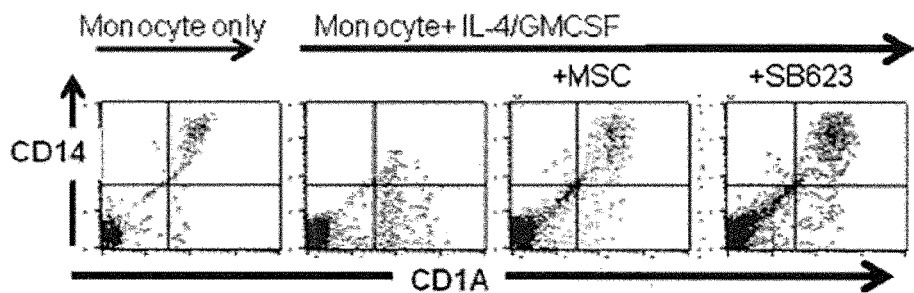
FIGS. 18A and 18B show levels of CD1a and CD14 in monocyte cultures after 7 days of culture or co-culture.
Figure 18B:
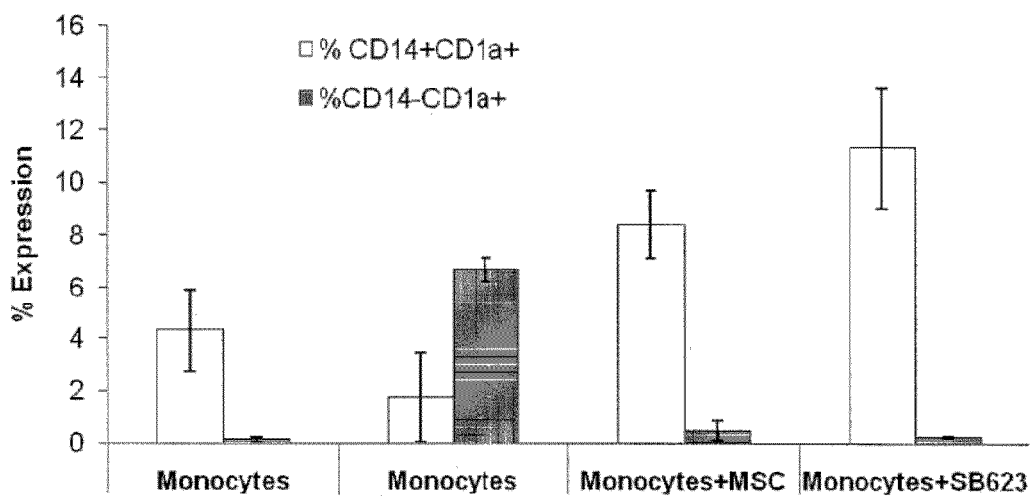

The results of the cell sorting analysis (FIGS. 18A and 18B) indicated a higher percentage of CD14+ cells (i.e., a higher fraction of monocytes) following co-culture of monocytes with SB623 cells or MSCs. Moreover, the effect was greater when monocytes were cultured with SB623 cells, compared to co-culture with MSCs. In addition, fewer CD1a+ dendritic cells were observed in the co-cultures. These results indicate that SB623 cells (and, to a lesser extent, MSCs) are able to block the differentiation of monocytes into dendritic cells.

Microscopic analysis confirmed these observations. In monocyte cultures, clusters of dendritic cells were readily observed by microscopy; but in co-cultures with MSCs or SB623 cells, such clusters were rarely observed.

Example 10: Inhibition of Dendritic Cell Maturation by Co-Culture with SB623 Cells After differentiating from monocytes, dendritic cells mature into a cell that expresses the CD86 surface marker. This maturation can be recapitulated in vitro by culturing dendritic cells in the presence of tumor necrosis factor-alpha (TNF-α). IL-6 and VEGF have been shown to block the maturation of dendritic cells. Park et al. (2004) J. Immunol. 173:3844-3854; Takahashi et al. (2004) Cancer Immunol. Immunother 53:543-550. Since SB623 cells secrete both of these cytokines, the effect of SB623 co-culture on dendritic cell differentiation was investigated.

To assess the effect of co-culture of SB623 cells on maturation of dendritic cells, monocytes were obtained from peripheral blood and differentiated in vitro into dendritic cells, as described in Example 9. After 5 days of culture, human (TNF-α (Peprotech, Rocky Hill, N.J.) was added to the cultures to a final concentration of 10 ng/ml. In some cultures, SB623 cells or MSCs were also added at this time. All samples contained $10^5$ monocytes and, in co-cultures, $10^4$ MSCs or SB623 cells. As a control, Cyclosporin A, which inhibits maturation of dendritic cells to a $CD86^+$ state, was added to TNF-α-stimulated cultures to a final concentration of 1 ug/ml. Two days later, cells were stained with PE-conjugated anti-CD86 antibodies (Becton Dickinson & Co., San Jose, Calif.), acquired on a FACSCalibur™ cell sorter and analyzed using CellQuest Pro™ software (both from Becton, Dickinson & Co., San Jose, Calif.).

Figure 19:
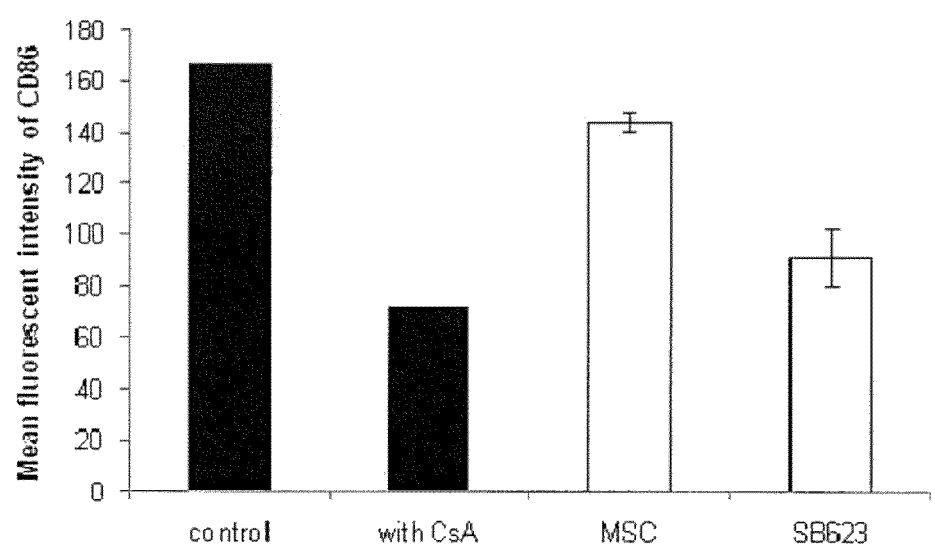
FIG. 19 shows levels of CD86, expressed as mean fluorescent intensity, in TNF-α-stimulated monocyte cultures. Cultures indicated by "Control" contained PBMCs cultured for five days in the presence of IL-4 and GM-CSF, then for a further 48 hours in TNF-α. Cultures indicated as "with CsA" contained PBMCs cultured for five days in the presence of IL-4 and GM-CSF, then for a further 48 hours in TNF-α+1 ug/ml cyclosporine A. Cultures indicated as "MSC" contained PBMCs cultured for five days in the presence of IL-4 and GM-CSF, then for a further 48 hours in TNF-α+$10^4$ MSCs. Cultures indicated as "SB623" contained PBMCs cultured for five days in the presence of IL-4 and GM-CSF, then for a further 48 hours in TNF-α+$10^4$ SB623 cells. The results for MSCs and SB623 cells are the average of three experiments, each using a sample from a different donor. Monocyte donor was the same in all cases. All cultures were started with $10^5$ PBMCs.

The results, shown in FIG. 19, indicate that a significant fraction of TNF-α-matured dendritic cells express CD86, and that this fraction is lowered by treatment with Cyclosporine A, as expected. Co-culture with SB623 cells and MSCs also lowers the fraction of $CD86^+$ cells. Notably, SB623 cells had a stronger inhibitory effect on dendritic cell maturation, as measured by CD86 expression, than did MSCs.

Example 11: Alteration of the Secretory Profile of Monocytes/Macrophages by Co-Culture with SB623 Cells Human peripheral blood monocytes expressing the CD14 cell surface marker (i.e., macrophage precursors) were obtained from cells of the buffy coat by magnetic selection, using anti-CD14-coated magnetic beads (Miltenyi Biotec, Auburn, Calif.). Separate cultures of the CD $14^+$ monocytes were exposed to granulocyte/macrophage colony-stimulating factor (GM-CSF), which converts them to M1 (pro-inflammatory) macrophages; or to macrophage colony-stimulating factor (M-CSF), which converts them to M2 (anti-inflammatory) macrophages; or were co-cultured with either SB623 cells or MSCs.

The percentage of cells expressing tumor necrosis factor-alpha (TNF-α, a pro-inflammatory cytokine characteristic of M1 macrophages) and interleukin 10 (IL-10, an anti-inflammatory cytokine characteristic of M2 macrophages) were determined in these cultures, as follows. Cultures were exposed to 100 ng/ml bacterial lipopolysaccharide (LPS, Sigma, St. Louis, Mo.) for 24 hours. During the final 6 hours of exposure to LPS, Brefeldin A and monensin (both from eBioscience San Diego, Calif.; and both used at 1:1,000 dilution) were added to the cultures. Cells were then stained with either PE-conjugated anti-TNF-α or FITC-conjugated anti-IL-10 and analyzed by flow cytometry.

Figure 20A:
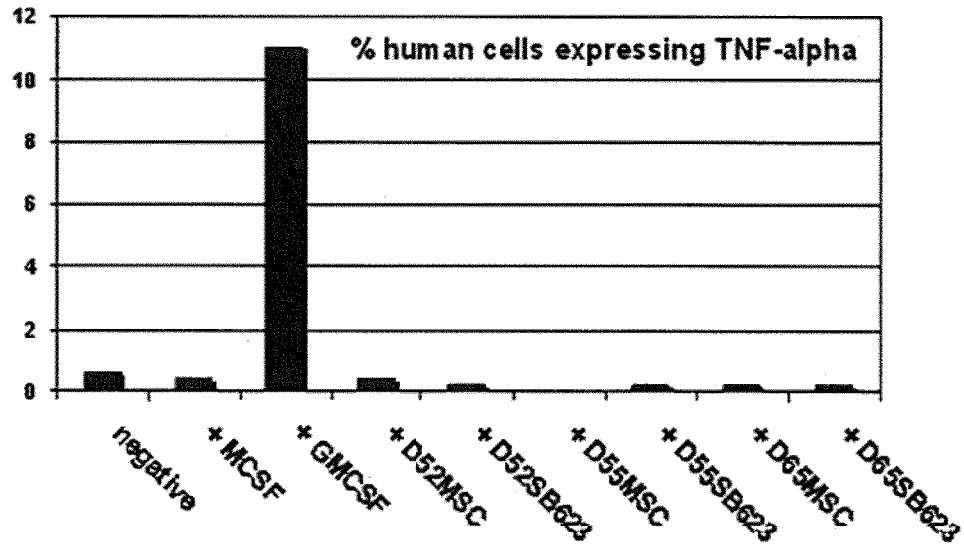
FIGS. 20A and 20B show measurements of cytokine expression in monocytes.
Figure 20B:
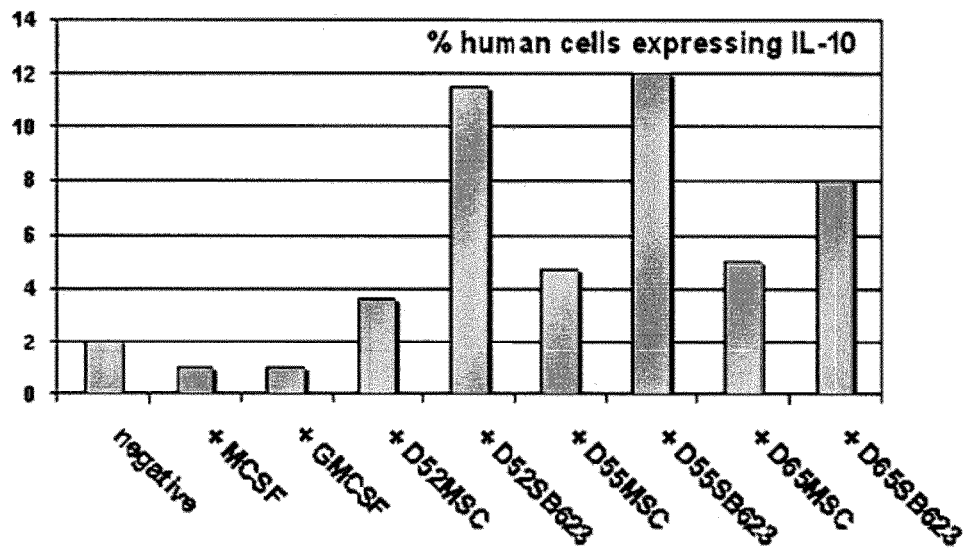

The results of these studies, shown in FIGS. 20A and 20B, indicated that coculture with MSCs or SB623 cells increased the fraction of monocytes in the culture that produced anti-inflammatory cytokines. Co-culture with MSCs or SB623 cells did not increase the percentage of cells that produced TNF-α, as did exposure to GM-CSF (FIG. 20A). Notably, the percentage of cells expressing the anti-inflammatory cytokine IL-10 was increased when monocytes were co-cultured with MSCs, and was increased even further when monocytes were co-cultured with SB623 cells (FIG. 20B).

We claim:

1. A method for suppressing the function of a $T_H1$ helper T cell in a subject, the method comprising:
    administering to the subject an effective amount of cells, wherein the cells are obtained by a method comprising:
    (a) providing a culture of mesenchymal stem cells;
    (b) contacting the cell culture of step (a) with a polynucleotide comprising sequences encoding a Notch intracellular domain (NICD) wherein said polynucleotide does not encode a full-length Notch protein;
    (c) selecting cells that comprise the polynucleotide of step (b); and
    (d) further culturing the selected cells of step (c) in the absence of selection for the polynucleotide;
    wherein the function is selected from one or more of:
    (i) activation of macrophages,
    (ii) activation of cytotoxic T-cells,
    (iii) activation of B cells,
    (iv) secretion of interferon gamma (IFN-γ), and
    (v) secretion of tumor necrosis factor alpha (TNF-α).

2. The method of claim 1, wherein the function is activation of macrophages.

3. The method of claim 1, wherein the function is activation of cytotoxic T cells.

4. The method of claim 1, wherein the function is activation of B cells.

5. The method of claim 1, wherein the function is secretion of interferon gamma (IFN-γ).

6. The method of claim 1, wherein the function is secretion of tumor necrosis factor alpha (TNF-α).

7. A method for suppressing the function of a $T_H2$ helper T cell in a subject, the method comprising:
    administering to the subject an effective amount of cells, wherein the cells are obtained by a method comprising:
    (a) providing a culture of mesenchymal stem cells;
    (b) contacting the cell culture of step (a) with a polynucleotide comprising sequences encoding a Notch intracellular domain (NICD) wherein said polynucleotide does not encode a full-length Notch protein;
    (c) selecting cells that comprise the polynucleotide of step (b); and
    (d) further culturing the selected cells of step (c) in the absence of selection for the polynucleotide;
    wherein the function is selected from one or more of:
    (i) activation of antibody production by B-cells,
    (ii) secretion of interleukin 4 (IL-4), and
    (iii) secretion of interleukin 10 (IL-10).

8. The method of claim 7, wherein the function is activation of antibody production by B cells.

9. The method of claim 7, wherein the function is secretion of interleukin 4 (IL-4).

10. The method of claim 7, wherein the function is secretion of interleukin 10 (IL-10).

* * * * *